US012004574B2

(12) United States Patent
Moloney et al.

(10) Patent No.: US 12,004,574 B2
(45) Date of Patent: Jun. 11, 2024

(54) DATA CAPTURE ACROSS DEVICES

(71) Applicant: NICOVENTURES TRADING LIMITED, London (GB)

(72) Inventors: Patrick Moloney, London (GB); Robert Kersey, London (GB); Darryl Baker, London (GB)

(73) Assignee: NICOVENTURES TRADING LIMITED, London (GB)

( * ) Notice: Subject to any disclaimer, the term of this patent is extended or adjusted under 35 U.S.C. 154(b) by 388 days.

(21) Appl. No.: 15/733,324

(22) PCT Filed: Dec. 21, 2018

(86) PCT No.: PCT/EP2018/086791
§ 371 (c)(1),
(2) Date: Jun. 26, 2020

(87) PCT Pub. No.: WO2019/129751
PCT Pub. Date: Jul. 4, 2019

(65) Prior Publication Data

US 2020/0329356 A1 Oct. 15, 2020

(30) Foreign Application Priority Data

Dec. 29, 2017 (GB) ..................................... 1722241

(51) Int. Cl.
*A24F 40/65* (2020.01)
*A24F 15/01* (2020.01)
(Continued)

(52) U.S. Cl.
CPC .............. *A24F 40/65* (2020.01); *A24F 15/01* (2020.01); *A61M 11/042* (2014.02);
(Continued)

(58) Field of Classification Search
None
See application file for complete search history.

(56) References Cited

U.S. PATENT DOCUMENTS

| | | |
|---|---|---|
| 6,196,218 B1 | 3/2001 | Voges |
| 8,061,361 B2 | 11/2011 | Maeder et al. |

(Continued)

FOREIGN PATENT DOCUMENTS

| | | |
|---|---|---|
| CN | 1631013 A | 6/2005 |
| CN | 1633780 A | 6/2005 |

(Continued)

OTHER PUBLICATIONS

International Search Report and Written Opinion, Application No. PCT/EP2018/086791, dated Feb. 13, 2019, 14 pages.

(Continued)

*Primary Examiner* — James Harvey
(74) *Attorney, Agent, or Firm* — BURR & FORMAN LLP

(57) ABSTRACT

The present disclosure teaches provision of a method for an aerosol provision device. The method includes operating a wireless communication interface of the aerosol provision device in a listening mode. During operation of the listening mode, data is received data from the wireless communication interface of another aerosol provision device. The received data is stored in a memory of the aerosol provision device. A connectionless-state advertising packet that includes information relating to an identity and advertising state of the aerosol provision device is created using the wireless communication interface of the aerosol provision device and transmitted via the wireless communication interface. A connectionless-state request packet is received from a remote wireless device, via the wireless communication interface. In response to receiving the request packet, a connectionless-state response packet is created using the
(Continued)

wireless communication interface and the response packet is transmitted via the wireless communication interface. At least one of the advertising packet and the response packet includes the received data from the memory and data generated by the aerosol provision device and stored in the memory.

14 Claims, 6 Drawing Sheets

(51) Int. Cl.
*A61M 11/04* (2006.01)
*A61M 15/06* (2006.01)
*H04W 4/80* (2018.01)
*H04W 8/00* (2009.01)

(52) U.S. Cl.
CPC .............. *A61M 15/06* (2013.01); *H04W 4/80* (2018.02); *H04W 8/005* (2013.01)

(56) References Cited

U.S. PATENT DOCUMENTS 9,254,007 B2 2/2016 Liu
9,642,167 B1 5/2017 Snyder et al.
10,097,387 B1 10/2018 Wiser et al.
10,258,087 B2 4/2019 Kane
10,349,675 B2 7/2019 Choukroun et al.
11,213,638 B2 1/2022 Nettenstrom et al.
11,388,931 B2 7/2022 Potter et al.
11,510,040 B2 11/2022 Kersey et al.
2004/0047319 A1 3/2004 Elg
2005/0117066 A1 6/2005 Kamijo
2011/0005535 A1 1/2011 Xiu
2011/0021142 A1 1/2011 Desai et al.
2011/0265806 A1 11/2011 Alarcon et al.
2012/0196534 A1 8/2012 Kasslin et al.
2013/0065584 A1 3/2013 Lyon et al.
2013/0081642 A1 4/2013 Safari
2013/0087160 A1 4/2013 Gherghe
2013/0178160 A1 7/2013 Wang
2013/0228191 A1 9/2013 Newton
2013/0263869 A1 10/2013 Zhu
2013/0276799 A1 10/2013 Davidson et al.
2013/0284192 A1 10/2013 Peleg et al.
2013/0306065 A1 11/2013 Thorens et al.
2013/0340775 A1 12/2013 Juster et al.
2014/0020697 A1 1/2014 Liu
2014/0060528 A1 3/2014 Liu
2014/0107815 A1 4/2014 Lamothe
2014/0123989 A1 5/2014 Lamothe
2014/0130816 A1 5/2014 Liu
2014/0169599 A1 6/2014 Solum et al.
2014/0174459 A1 6/2014 Burstyn
2014/0202477 A1 7/2014 Qi et al.
2014/0238423 A1 8/2014 Tucker et al.
2014/0238424 A1 8/2014 Macko et al.
2014/0278250 A1 9/2014 Smith et al.
2014/0378057 A1 12/2014 Ramon et al.
2014/0378790 A1 12/2014 Cohen
2015/0040927 A1 2/2015 Li et al.
2015/0099469 A1 4/2015 Goldstein
2015/0101625 A1 4/2015 Newton et al.
2015/0101940 A1 4/2015 Ash
2015/0133054 A1 5/2015 Chen et al.
2015/0134619 A1 5/2015 Factor et al.
2015/0142387 A1 5/2015 Alarcon et al.
2015/0144145 A1 5/2015 Chang et al.
2015/0172391 A1 6/2015 Kasslin et al.
2015/0216237 A1 8/2015 Wensley et al.
2015/0224268 A1 8/2015 Henry et al.
2015/0272220 A1 10/2015 Spinka et al.
2015/0312858 A1 10/2015 Kerai
2015/0313283 A1 11/2015 Collett et al.
2015/0319555 A1 11/2015 Cordeiro et al.
2015/0327596 A1 11/2015 Alarcon et al.
2015/0358759 A1 12/2015 Jakusovszky et al.
2016/0015081 A1 1/2016 Liu
2016/0015082 A1 1/2016 Liu
2016/0021488 A1 1/2016 Viswanadham et al.
2016/0029148 A1 1/2016 Jackson et al.
2016/0029149 A1 1/2016 Morikawa et al.
2016/0037012 A1 2/2016 Okado
2016/0037566 A1 2/2016 Jakusovszky et al.
2016/0073692 A1 3/2016 Alarcon et al.
2016/0089508 A1 3/2016 Smith et al.
2016/0100276 A1 4/2016 Viswanadham et al.
2016/0100311 A1 4/2016 Kumar
2016/0105761 A1 4/2016 Polo et al.
2016/0121058 A1 5/2016 Chen
2016/0184635 A1 6/2016 Kwon
2016/0191642 A1 6/2016 Acar
2016/0262451 A1 9/2016 Liu
2016/0278163 A1 9/2016 Chen
2016/0278435 A1 9/2016 Choukroun et al.
2016/0286863 A1 10/2016 Lin
2016/0316819 A1 11/2016 Zhou et al.
2016/0338407 A1 11/2016 Kerdemelidis
2016/0345632 A1 12/2016 Lipowicz
2016/0353798 A1 12/2016 Liu
2016/0353800 A1 12/2016 Di Carlo
2016/0363570 A1 12/2016 Blackley
2016/0363917 A1 12/2016 Blackley
2016/0374133 A1 12/2016 Logue et al.
2017/0020188 A1 1/2017 Cameron
2017/0026905 A1 1/2017 Denboer et al.
2017/0041381 A1 2/2017 Tal et al.
2017/0041868 A1 2/2017 Palin et al.
2017/0042242 A1 2/2017 Hon
2017/0071262 A1 3/2017 Liu
2017/0093960 A1 3/2017 Cameron
2017/0093981 A1 3/2017 Cameron
2017/0118292 A1 4/2017 Xiang
2017/0127725 A1 5/2017 Buchberger et al.
2017/0193816 A1 7/2017 Lee et al.
2017/0223604 A1 8/2017 Skillermark et al.
2017/0258136 A1 9/2017 Hawes et al.
2017/0273358 A1 9/2017 Batista et al.
2017/0273359 A1 9/2017 Liu
2017/0303596 A1 10/2017 Chen
2018/0062868 A1 3/2018 Higo et al.
2018/0132102 A1 5/2018 Kwon et al.
2018/0270311 A1 9/2018 Baker et al.
2018/0270643 A1 9/2018 Baker et al.
2018/0280640 A1 10/2018 Baker et al.
2018/0286208 A1 10/2018 Baker et al.
2018/0303163 A1 10/2018 Baker et al.
2019/0286456 A1 9/2019 Baker et al.
2020/0029371 A1 1/2020 Achtien et al.
2020/0060347 A1 2/2020 Kersey et al.
2020/0178607 A1 6/2020 Blick et al.
2020/0237014 A1 7/2020 Lee et al.
2020/0315254 A1 10/2020 Zielazek et al.
2020/0329356 A1* 10/2020 Moloney ................. H04W 4/80
2020/0352238 A1 11/2020 Simpson et al.
2021/0145055 A1 5/2021 Potter et al.
2021/0251300 A1 8/2021 Jung et al.
2021/0308392 A1 10/2021 Alarcon et al.
2022/0060873 A1 2/2022 Kersey et al.
2022/0095688 A1* 3/2022 Talbot ..................... A24F 40/53

FOREIGN PATENT DOCUMENTS

CN 101800575 A 8/2010
CN 102035574 A 4/2011
CN 201781984 U 4/2011
CN 201830900 U 5/2011
CN 102684753 A 9/2012
CN 102970885 A 3/2013
CN 103380952 A 11/2013
CN 103798960 A 5/2014
CN 103914013 A 7/2014
CN 203913385 U 11/2014

(56) References Cited

FOREIGN PATENT DOCUMENTS

| | | | |
|---|---|---|---|
| CN | 204120237 | U | 1/2015 |
| CN | 104366695 | A | 2/2015 |
| CN | 104412629 | A | 3/2015 |
| CN | 104488348 | A | 4/2015 |
| CN | 204351068 | U | 5/2015 |
| CN | 104664605 | A | 6/2015 |
| CN | 104720117 | A | 6/2015 |
| CN | 104811895 | A | 7/2015 |
| CN | 204426699 | U | 7/2015 |
| CN | 204483034 | U | 7/2015 |
| CN | 204483035 | U | 7/2015 |
| CN | 104955508 | A | 9/2015 |
| CN | 104980284 | A | 10/2015 |
| CN | 105163614 | A | 12/2015 |
| CN | 105188428 | A | 12/2015 |
| CN | 105208882 | A | 12/2015 |
| CN | 105210420 | A | 12/2015 |
| CN | 105310114 | A | 2/2016 |
| CN | 105342010 | A | 2/2016 |
| CN | 105433442 | A | 3/2016 |
| CN | 205285008 | U | 6/2016 |
| CN | 205512338 | U | 8/2016 |
| CN | 205624465 | U | 10/2016 |
| CN | 106102811 | A | 11/2016 |
| CN | 106376976 | A | 2/2017 |
| CN | 106535682 | A | 3/2017 |
| CN | 106604655 | A | 4/2017 |
| CN | 206119177 | U | 4/2017 |
| CN | 206197019 | U | 5/2017 |
| CN | 206197020 | U | 5/2017 |
| CN | 107251583 | A | 10/2017 |
| CN | 107301020 | A | 10/2017 |
| CN | 107708452 | A | 2/2018 |
| CN | 108028859 | A | 5/2018 |
| EP | 1357712 | A1 | 10/2003 |
| EP | 1494403 | A3 | 9/2009 |
| EP | 2110034 | A1 | 10/2009 |
| EP | 2460424 | A1 | 6/2012 |
| EP | 2533477 | A1 | 12/2012 |
| EP | 2533477 | B1 | 3/2014 |
| EP | 2739020 | A2 | 6/2014 |
| EP | 2823720 | A1 | 1/2015 |
| EP | 2959784 | A1 | 12/2015 |
| EP | 2984952 | A1 | 2/2016 |
| EP | 3062643 | A1 | 9/2016 |
| EP | 3108759 | A1 | 12/2016 |
| GB | 2513639 | A | 11/2014 |
| GB | 2521224 | A | 6/2015 |
| JP | 2001352377 | A | 12/2001 |
| JP | 2002044730 | A | 2/2002 |
| JP | 2002247097 | A | 8/2002 |
| JP | 2002252616 | A | 9/2002 |
| JP | 2003229782 | A | 8/2003 |
| JP | 2005159821 | A | 6/2005 |
| JP | 2005236819 | A | 9/2005 |
| JP | 2007036421 | A | 2/2007 |
| JP | 2009252002 | A | 10/2009 |
| JP | 2013524835 | A | 6/2013 |
| JP | 2014110635 | A | 6/2014 |
| JP | 2014110637 | A | 6/2014 |
| JP | 2015180214 | A | 10/2015 |
| JP | 2017514504 | A | 6/2017 |
| JP | 2017169185 | A | 9/2017 |
| JP | 2018032269 | A | 3/2018 |
| JP | 2018533924 | A | 11/2018 |
| JP | 2018536309 | A | 12/2018 |
| JP | 2020526222 | A | 8/2020 |
| JP | 2021506296 | A | 2/2021 |
| JP | 2021523685 | A | 9/2021 |
| KR | 20020057207 | A | 7/2002 |
| KR | 20120098343 | A | 9/2012 |
| KR | 20140002774 | U | 5/2014 |
| KR | 20150032188 | A | 3/2015 |
| KR | 101570106 | B1 | 11/2015 |
| KR | 20150140584 | A | 12/2015 |
| KR | 20160009678 | A | 1/2016 |
| KR | 101609715 | B1 | 4/2016 |
| RU | 2420901 | C2 | 6/2011 |
| RU | 2425608 | C2 | 8/2011 |
| RU | 2011120430 | A | 11/2012 |
| RU | 2509516 | C2 | 3/2014 |
| RU | 2536166 | C2 | 12/2014 |
| RU | 2598568 | C2 | 9/2016 |
| RU | 2606572 | C2 | 1/2017 |
| RU | 2620754 | C2 | 5/2017 |
| RU | 2636917 | C2 | 11/2017 |
| RU | 2638917 | C2 | 12/2017 |
| RU | 2639972 | C2 | 12/2017 |
| TW | 201513524 | A | 4/2015 |
| TW | 201613524 | A | 4/2016 |
| WO | WO-2005057956 | A1 | 6/2005 |
| WO | 2011137453 | A2 | 11/2011 |
| WO | 2011146375 | A2 | 11/2011 |
| WO | WO-2014060269 | A1 | 4/2014 |
| WO | 2014088230 | A1 | 6/2014 |
| WO | WO-2014085719 | A1 | 6/2014 |
| WO | WO-2014150704 | A2 | 9/2014 |
| WO | WO-2014195805 | A2 | 12/2014 |
| WO | 2015063126 | A1 | 5/2015 |
| WO | WO-2015099751 | A1 | 7/2015 |
| WO | WO-2016017909 | A1 | 2/2016 |
| WO | 2016041209 | A1 | 3/2016 |
| WO | WO-2016037012 | A1 | 3/2016 |
| WO | 2016079151 | A1 | 5/2016 |
| WO | 2016090531 | A1 | 6/2016 |
| WO | WO-2016108646 | A1 | 7/2016 |
| WO | 2016176800 | A1 | 11/2016 |
| WO | WO-2016179271 | A1 | 11/2016 |
| WO | 2016190222 | A1 | 12/2016 |
| WO | 2016198417 | A1 | 12/2016 |
| WO | 2016207357 | A1 | 12/2016 |
| WO | 2016208756 | A1 | 12/2016 |
| WO | 2017001818 | A1 | 1/2017 |
| WO | 2017001819 | A1 | 1/2017 |
| WO | 2017015832 | A1 | 2/2017 |
| WO | WO-2017020188 | A1 | 2/2017 |
| WO | WO-2017051173 | A1 | 3/2017 |
| WO | WO2017051174 | | 3/2017 |
| WO | 2017055800 | A1 | 4/2017 |
| WO | WO-2017055795 | A1 | 4/2017 |
| WO | WO-2017055801 | A1 | 4/2017 |
| WO | WO-2017055802 | A1 | 4/2017 |
| WO | WO-2017203488 | A1 | 11/2017 |
| WO | 2017215221 | A1 | 12/2017 |
| WO | 2018202651 | A1 | 11/2018 |
| WO | 2019121778 | A1 | 6/2019 |

OTHER PUBLICATIONS

International Preliminary Report on Patentability, Application No. PCT/EP2018/086791, dated Mar. 12, 2020, 13 pages.

Application and File History for U.S. Appl. No. 15/733,324, filed Jun. 26, 2020, Inventor: Patrick Moloney et al.

Application and File History for U.S. Appl. No. 15/733,325, filed Jun. 26, 2020, Inventor: Darryl Baker et al.

Application and File History for U.S. Appl. No. 15/762,018, filed Mar. 21, 2018, 446 pages, Inventor: Baker.

Application and File History for U.S. Appl. No. 15/762,021, filed Mar. 21, 2018, Inventor: Baker, 442 pages.

Application and File History for U.S. Appl. No. 16/610,588, filed Nov. 4, 2019, Inventor: Otiaba et al., 242 pages.

Bluetooth, "Specification of the Bluetooth System: Experience More", Specification vol. 1, Covered Core Package version: 4.0, Jun. 30, 2010, 137 pages.

Bronzi W., et al., "Bluetooth Low Energy for Inter-Vehicular Communications", IEEE Vehicular Networking Conference, Dec. 3, 2014, pp. 215-221.

Decision of grant for Russian Application No. 2019134027 dated Aug. 18, 2020, 10 pages.

Decision to Grant dated Apr. 3, 2019 for Russian Application No. 201810957808, 12 pages.

(56) References Cited

OTHER PUBLICATIONS

Decision to Grant dated Dec. 13, 2018 for Russian Application No. 201810978608, 10 pages.
Examination Report No. 1 dated Jun. 1, 2021 for New Zealand Application No. 765016, 4 pages.
Extended European Search Report for Application No. 20204701.5, dated Jan. 28, 2021, 8 pages.
Extended European Search Report for Application No. 21201390.8, dated Jan. 28, 2022, 9 pages.
IEEE 802.11, IEEE Standard, 2 pages, as retrieved on Feb. 19, 2018.
IEEE 802.15.1 WPAN Task Group 1 (TG1), available at https://www.ieee802.org/15/pub/TGI.html, Mar. 15, 2016, 2 pages.
IEEE Standard for Local Metropolitan Area Networks, Part 15.4: Low-Rate Wireless Personal Area Networks (LR-WPANs), IEEE Std 802.15.4, Sep. 5, 2011, 314 pages.
International Preliminary Report on Patentability for Application No. PCT/EP2018/061086, dated Oct. 10, 2019, 15 pages.
International Preliminary Report on Patentability for Application No. PCT/EP2018/086624, dated Mar. 16, 2020, 15 pages.
International Preliminary Report on Patentability for Application No. PCT/GB2016/052939, dated Sep. 14, 2017, 9 pages.
International Preliminary Report on Patentability for Application No. PCT/GB2016/052940, dated Sep. 14, 2017, 8 pages.
International Search Report and Written Opinion for Application No. PCT/EP2018/061086, dated Jul. 11, 2018, 14 pages.
International Search Report and Written Opinion for Application No. PCT/EP2018/086624, dated Feb. 11, 2019, 13 pages.
International Search Report and Written Opinion for Application No. PCT/GB2016/052939, dated Nov. 18, 2016, 17 pages.
International Search Report and Written Opinion for Application No. PCT/GB2016/052940, dated Dec. 8, 2016, 12 pages.
Liu Y., et al., "A Bluetooth Scatternet-Route Structure for Multihop Ad Hoc Networks", IEEE Journal on Selected Areas in Communications, Feb. 1, 2003, vol. 21 No. 2, pp. 229-239.
Notice of Reasons for Refusal dated Nov. 24, 2021 for Japanese Application No. 2020-183041, 8 pages.
Office Action dated Nov. 21, 2019 for Chinese Application No. 201680047153.9, 12 pages.
Office Action for Application No. 16775827.5, dated Jan. 28, 2019, 5 pages.
Office Action for Chinese Application No. 201880029165.8, dated Mar. 16, 2022, 16 pages.
Office Action for Japanese Application No. 2018-513274, dated Jan. 31, 2019, 2 pages (4 pages with translation).
Office Action for Japanese Application No. 2018-513357, dated Jan. 29, 2019, 3 pages (7 pages with translation).
Office Action for Japanese Application No. 2020-530641, dated Aug. 17, 2021, 5 pages.
Office Action for Japanese Application No. 2020-531510, dated Sep. 21, 2021, 5 pages.
Office action for Japanese Application No. 2021-169568, dated Aug. 23, 2022, 16 pages.
Office action for Korean Application No. 10-2022-7001663, dated Aug. 10, 2022, 12 pages.
Office Action for Russian Application No. 2020120938, dated Nov. 11, 2020, 13 pages.
Office Action for Russian Application No. 2020121494, dated Nov. 18, 2020, 6 pages.
Office Action for Russian Application No. 2020135708, dated May 24, 2021, 16 pages.
Office Action dated May 11, 2022 for Russian Application No. 2021132532, 12 pages.
Office Action dated Nov. 15, 2021 for Japanese Application No. 2020-183041, 42 pages.
Office Action dated Apr. 21, 2021 for Korean Application No. 10-2020-7018465, 11 pages.
Office Action dated Jul. 30, 2020 for Korean Application No. 10-2019-7032414 filed Oct. 31, 2019, 11 pages.
Partial Search Report dated Feb. 18, 2016 for Great Britain Application No. GB1516673.9, 4 pages.
Search Report dated Dec. 13, 2018 for Russian Application No. 201810978608, 2 pages.
Search Report dated Feb. 18, 2016 for Great Britain Application No. GB1516674.7, 5 pages.
Second Written Opinion for Application No. PCT/EP2018/061086, dated Jul. 23, 2019, 8 pages.
Written Opinion for Application No. PCT/EP2018/061086, dated Apr. 10, 2019, 8 pages.
Written Opinion of International Preliminary Authority for Application No. PCT/EP2018/086624, dated Nov. 25, 2019, 6 pages.
"Examination Report No. 1 received for Australian Patent Application No. 2021254534, mailed on Oct. 5, 2022", 3 Pages.
"Notice of Allowance received for Korean Patent Application No. 10-2022-7001663, mailed on Feb. 16, 2023", 6 pages (3 pages of English Translation and 3 pages of Official Copy).
"Notice of Allowance received for Korean Patent Application No. 10-2022-7001975, mailed on Feb. 16, 2023", 4 pages (1 page of English Translation and 3 pages of Official Copy).
"Notice of Reasons for Rejection received for Japanese Patent Application No. 2021-148436, mailed on Nov. 29, 2022", 8 pages (4 pages of English Translation and 4 pages of Official Copy).
"Office Action and Search Report received for Chinese Application No. 2018800844162, mailed Dec. 22, 2022", 17 pages (8 pages of English Translation and 9 pages of Official Copy).
"Office Action received for Russian Patent Application No. 2022114546, mailed on Nov. 18, 2022", 6 pages (Official Copy Only).
Moloney, Patrick , et al., "Application and File History for U.S. Appl. No. 16/610,587, filed Nov. 4, 2019".
Communication pursuant to Article 94(3) EPC for European Patent Application No. 18715070.1, mailed on Aug. 4, 2022, 6 pages.
Communication pursuant to Article 94(3) EPC for European Patent Application No. 18715070.1, mailed on Nov. 2, 2020, 21 pages.
Decision to Grant received for Japanese Patent Application No. 2020-537201, mailed on Jul. 13, 2021, 5 pages (2 pages of English Translation and 3 pages Official Copy).
International Preliminary Report on Patentability received for PCT Patent Application No. PCT/GB2018/050726, mailed on Jul. 3, 2019, 32 pages.
International Preliminary Report on Patentability received for PCT Patent Application No. PCT/GB2019/050037, mailed on May 8, 2020, 21 pages.
International Preliminary Report on Patentability received for PCT Patent Application No. PCT/GB2019/050186, mailed on May 8, 2020, 8 pages.
International Preliminary Report on Patentability received for PCT Patent Application No. PCT/GB2019/050187, mailed on Aug. 6, 2020, 8 pages.
International Search Report and Written Opinion received for PCT Patent Application No. PCT/GB2018/050726, mailed on Jun. 12, 2018, 15 pages.
International Search Report and Written Opinion received for PCT Patent Application No. PCT/GB2019/050037, mailed on Mar. 25, 2019, 12 pages.
International Search Report and Written Opinion received for PCT Patent Application No. PCT/GB2019/050089, mailed on Mar. 25, 2019, 10 pages.
International Search Report received for PCT Patent Application No. PCT/GB2019/050187, mailed on Apr. 18, 2019, 3 pages.
Notice of Allowance received for Korean Patent Application No. 10-2020-7021264, mailed on Nov. 14, 2022, 6 pages (3 pages of English Translation and 3 pages of Official Copy).
Office Action received for Canadian Patent Application No. 3089292, mailed on Dec. 16, 2021, 6 pages.
Office Action received for Chinese Patent Application No. 201880020522.4, mailed on Aug. 3, 2021, 29 pages (15 Pages of English Translation and 14 Pages of Official Copy).
Office Action received for Chinese Patent Application No. 201880020522.4, mailed on May 20, 2022, 12 pages (10 pages of English Translation and 2 pages of Official Copy).
Office Action received for Chinese Patent Application No. 201980009907.5, mailed on Nov. 2, 2022, 17 pages (9 pages of English Translation and 8 pages of Official Copy).

(56) References Cited

OTHER PUBLICATIONS

Office Action received for Russian Patent Application No. 2020124567, mailed on Jan. 28, 2021, 2 pages (Official Copy Only).
Reason of Refusal received for Korean Patent Application No. 10-2019-7027899, mailed on Jan. 18, 2021, 17 pages (9 pages of English Translation and 8 pages of Official Copy).
Reasons for Refusal received for Korean Patent Application No. 10-2019-7027899, mailed on Jul. 27, 2021, 15 pages (8 pages of English Translation and 7 pages of Official Copy).
Reasons for Rejection received for Japanese Patent Application No. 2020-539826, mailed on Jun. 15, 2021, 14 pages (7 pages of English Translation and 7 pages of Official Copy).
Search Report received for Great Britain Patent Application No. GB 1702861.4, mailed on May 31, 2017, 5 pages.
Search Report received for Great Britain Patent Application No. GB 1704674.9, mailed on Apr. 27, 2017, 5 pages.
Search Report received for Russian Patent Application No. 2020124379, mailed on Mar. 2, 2021, 2 pages (Official Copy Only).
Second Office Action received for Chinese Patent Application No. 201880020522.4, mailed on Jan. 20, 2022, 17 pages (7 pages of English Translation and 10 pages of Official Copy).
Harry, "What's the Difference Between an Atomizer, Cartomizer and Clearomizer?", Vaporesso, Available at <https://www.vaporesso.com/blog/difference-between-an-atomizer-cartomizer-and-clearomizer>, Aug. 7, 2019, 6 pages.
Extended Europe Search Report issued in corresponding European Application No. 23204201.0 on Feb. 6, 2024, all enclosed pages cited.

* cited by examiner

```
                              Start
                                │
                                ▼                              S9-1
      ┌──────────────────────────────────────────────────┐
      │  Operate the wireless communication interface of  │
      │       the aerosol provision device in a listening │
      │                       mode                        │
      └──────────────────────────────────────────────────┘
                                │
                                ▼                              S9-2
      ┌──────────────────────────────────────────────────┐
      │  Receive data from the wireless communication     │
      │    interface of another aerosol provision device  │
      └──────────────────────────────────────────────────┘
                                │
                                ▼                              S9-3
      ┌──────────────────────────────────────────────────┐
      │  Store the received data in the memory of the     │
      │             aerosol provision device              │
      └──────────────────────────────────────────────────┘
                                │
                                ▼                              S9-4
      ┌──────────────────────────────────────────────────┐
      │  Create, using the wireless communication         │
      │  interface of the aerosol delivery device, a      │
      │  connectionless-state advertising packet that     │
      │  includes information relating to an identity and │
      │  advertising state of the aerosol delivery device │
      └──────────────────────────────────────────────────┘
                                │
                                ▼                              S9-5
      ┌──────────────────────────────────────────────────┐
      │  Transmit the advertising packet via the wireless │
      │                communication interface            │
      └──────────────────────────────────────────────────┘
                                │
                                ▼                              S9-6
      ┌──────────────────────────────────────────────────┐
      │  Receive a connectionless-state request packet    │
      │  from a remote wireless device, via the wireless  │
      │             communication interface               │
      └──────────────────────────────────────────────────┘
                                │
                                ▼                              S9-7
      ┌──────────────────────────────────────────────────┐
      │  Create, using the wireless communication         │
      │  interface, a connectionless state response packet│
      └──────────────────────────────────────────────────┘
                                │
                                ▼                              S9-8
      ┌──────────────────────────────────────────────────┐
      │  Transmit the response packet via the wireless    │
      │              communication interface              │
      └──────────────────────────────────────────────────┘
                                │
                                ▼
                              Stop
```

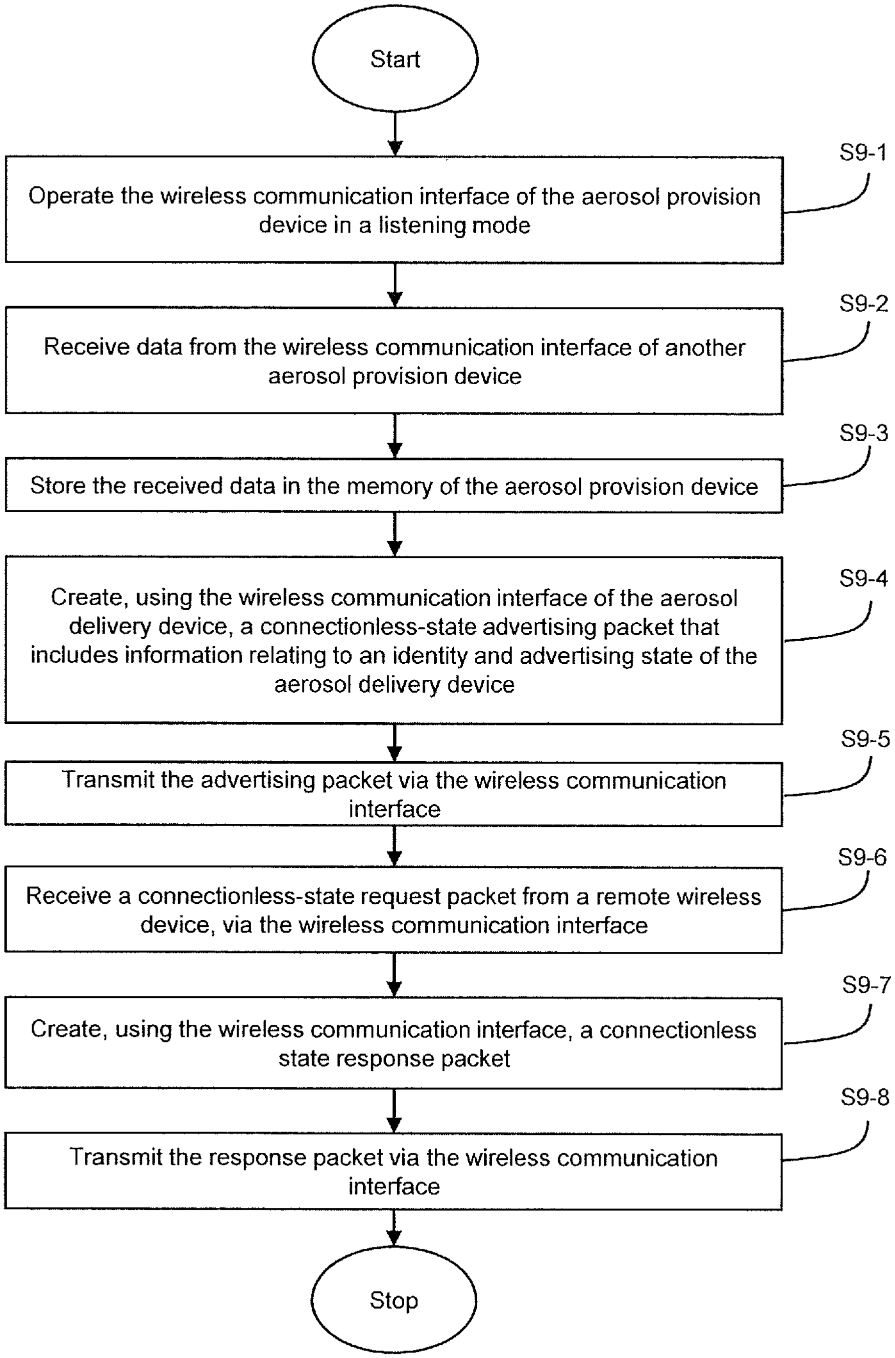

FIG. 9

DATA CAPTURE ACROSS DEVICES

PRIORITY CLAIM

The present application is a National Phase entry of PCT Application No. PCT/EP2018/086791, filed Dec. 21, 2018, which claims priority from Great Britain Patent Application No. 1722241.5, filed Dec. 29, 2017, each of which is hereby fully incorporated herein by reference.

TECHNICAL FIELD

The present disclosure relates to a method for an aerosol provision device and an aerosol provision device.

BACKGROUND

In conventional wireless communication approaches, such as Bluetooth and Bluetooth Low Energy (also known as Bluetooth Smart Technology), individual devices can be operated as nodes taking the role of masters or slaves in a particular communication relationship. Thus each node adopts the role of master or the role of slave. Accordingly, in a communication pair, one node acts as master and the other acts as slave. In the context of Bluetooth Low Energy, the master may be referred to as the central and the slave as the peripheral. One master (or central) node can be a master to several slaves (the exact number often limited by a particular chipset implementation) and although a node can be registered as a slave (or peripheral) to multiple masters, it can only be active as a slave to one master at any one time.

Bluetooth and Bluetooth Low Energy are fundamentally different in operation to other Low-rate wireless personal area networks (LR-WPANs) such as Zigbee™ and Thread™, which are both based upon the IEEE 802.15.4 wireless protocol.

Publications WO 2017/051173, U.S. 2017/118292, and U.S. 2017/093981 described examples of exchanging information between aerosol provision devices.

SUMMARY

Some specific aspects and embodiments are set out in the appended claims.

Viewed from a first aspect, there can be provided a method for an aerosol provision device comprising: operating a wireless communication interface of the aerosol provision device in a listening mode; during operation of the listening mode, receiving data from the wireless communication interface of another aerosol provision device; storing the received data in a memory of the aerosol provision device; creating, using the wireless communication interface of the aerosol provision device, a connectionless-state advertising packet that includes information relating to an identity and advertising state of the aerosol provision device; transmitting the advertising packet via the wireless communication interface; receiving a connectionless-state request packet from a remote wireless device, via the wireless communication interface; responsive to receiving the request packet, creating, using the wireless communication interface, a connectionless-state response packet; and transmitting the response packet via the wireless communication interface, wherein at least one of the advertising packet and the response packet includes the received data from the memory and data generated by the aerosol provision device and stored in the memory.

Viewed from another aspect, there can be provided an aerosol provision device comprising: a processor; a wireless communication interface; memory containing instructions which, when executed by the processor, performs the method of operating a wireless communication interface of the aerosol provision device in a listening mode; during operation of the listening mode, receiving data from the wireless communication interface of another aerosol provision device; storing the received data in a memory of the aerosol provision device; creating, using the wireless communication interface of the aerosol provision device, a connectionless-state advertising packet that includes information relating to an identity and advertising state of the aerosol provision device; transmitting the advertising packet via the wireless communication interface; receiving a connectionless-state request packet from a remote wireless device, via the wireless communication interface; responsive to receiving the request packet, creating, using the wireless communication interface, a connectionless-state response packet; and transmitting the response packet via the wireless communication interface, wherein at least one of the advertising packet and the response packet includes the received data from the memory and data generated by the aerosol provision device and stored in the memory.

BRIEF DESCRIPTION OF THE DRAWINGS

Embodiments of the present teachings will now be described, by way of example only, with reference to accompanying drawings, in which:

FIG. 9 schematically illustrates a method for an aerosol provision device.

Figure 1:
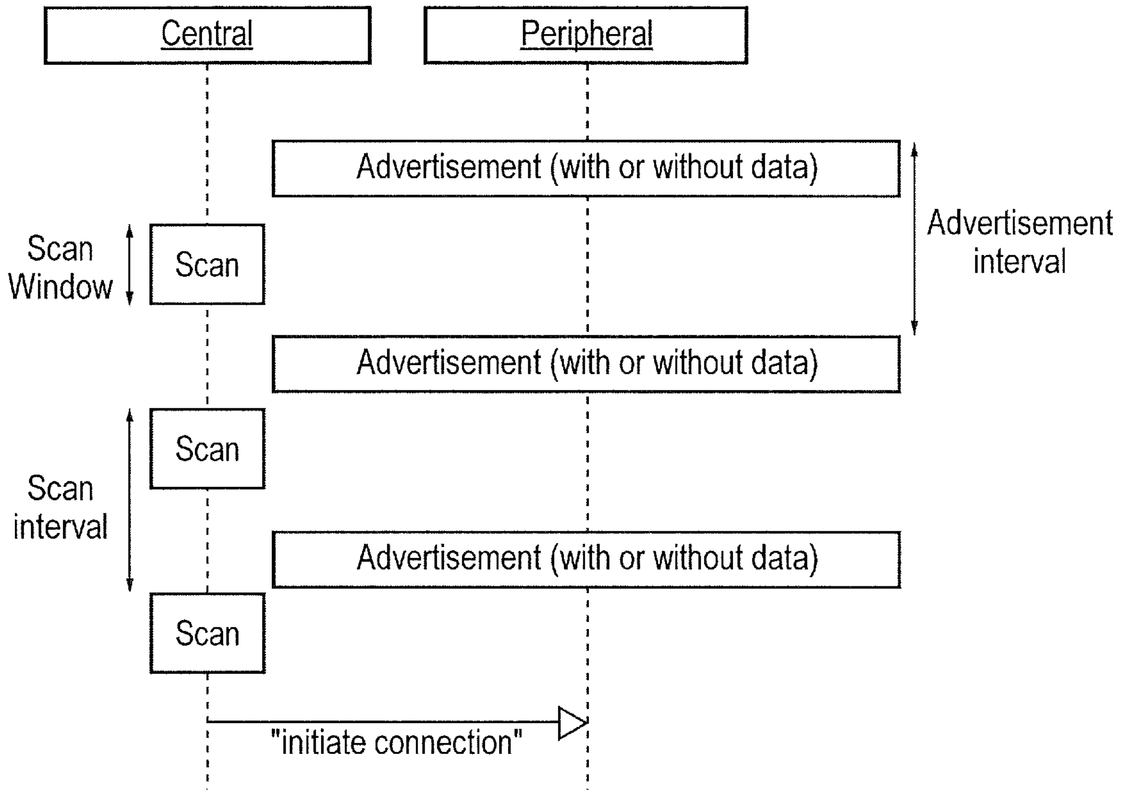
FIG. 1 schematically illustrates an advertising protocol.

While the presently described approach is susceptible to various modifications and alternative forms, specific embodiments are shown by way of example in the drawings and are herein described in detail. It should be understood, however, that drawings and detailed description thereto are not intended to limit the scope to the particular form disclosed, but on the contrary, the scope is to cover all modifications, equivalents and alternatives falling within the spirit and scope as defined by the appended claims.

DETAILED DESCRIPTION

The present disclosure relates to a modified form of wireless communication behavior. According to the present teachings, a device can be configured to use a Bluetooth or Bluetooth-like communications protocol and can, in a manner that may be transparent to other devices using the communications protocol for communication with the device, operate as both a master/central and a slave/peripheral in different communication relationships at the same time on a time division basis.

In some examples, the devices can be aerosol provision devices such as so-called "E-cigarettes", sometimes also known as Electronic Nicotine Delivery devices (END devices), provided with electronics that allow them to communicate with other communication devices. As used herein, the term "aerosol provision device" refers either to a device including an aerosol source material (e.g., a device part and a disposable cartomizer part containing the aerosol source material) and/or a device not including an aerosol source material (e.g., just the device part of the previous example).

In the present examples, the devices use Bluetooth Low Energy ("BTLE"), but other Bluetooth protocols or Bluetooth-like protocols can take advantage of the present teachings. Bluetooth is a wireless technology standard for short distance communication between appropriately enabled devices. BTLE is a variant on the original Bluetooth system, designed to draw less power in use for extended battery life and/or small battery applications. Both Bluetooth and BTLE operate in the UHF radio industrial, scientific and medical (ISM) band from 2.4 to 2.485 GHz and are designed for creating so-called wireless personal area networks (PANs) for interconnecting devices over short distances. BTLE uses a modified version of the Bluetooth stack for communication such that a BTLE device and a traditional Bluetooth device are not directly compatible unless one device implements both protocols. Both Bluetooth and BTLE standards are maintained by the Bluetooth Special Interest Group (SIG). The present disclosure is provided in the context of a BTLE implementation using the part of the Bluetooth v4 specification that relates to BTLE. However, the skilled reader will appreciate that the present teachings can be applied to other Bluetooth approaches, such as the so-called Classic Bluetooth definitions that are also set out in the Bluetooth v4 specification. It will be further appreciated that the present teachings can be applied to technologies that are not in accordance with an entire Bluetooth specification, but which nevertheless behave in a Bluetooth-like manner.

For example, non-Bluetooth systems that nevertheless use an advertising setup based on the Bluetooth Low Energy Generic Access Profile (GAP) and thus have an advertising structure substantially as set out in FIG. 1 would be able to deploy the techniques of the present teachings. FIG. 1 illustrates an advertising structure according to which a peripheral (or slave or remote or secondary) device advertises its availability as a peripheral (or slave or remote or secondary) device during an advertisement period, with the advertisement periods being separated by an advertisement interval. The advertisement may include data for transmission, an indication that there is data for transmission or have no data reference at all. To receive the advertisement, a central (or primary or control) device scans for advertisements during a scan window. Multiple scan windows are separated by a scan interval. The relative duration of the scan and advertisement intervals is altered, either by determining that the interval at one device type is constant while the other varies, or by determining that both vary, which determination can be set by a standard or rule set for implementing the advertising protocol. By providing this relative variation in the scan and advertisement intervals, it is provided that even where an initial advertisement period does not overlap with an initial scan window, after a number of advertisement and scan intervals, an advertisement period will occur which overlaps with a scan window such that a connection can be initiated between the central and the peripheral device.

Figure 2:
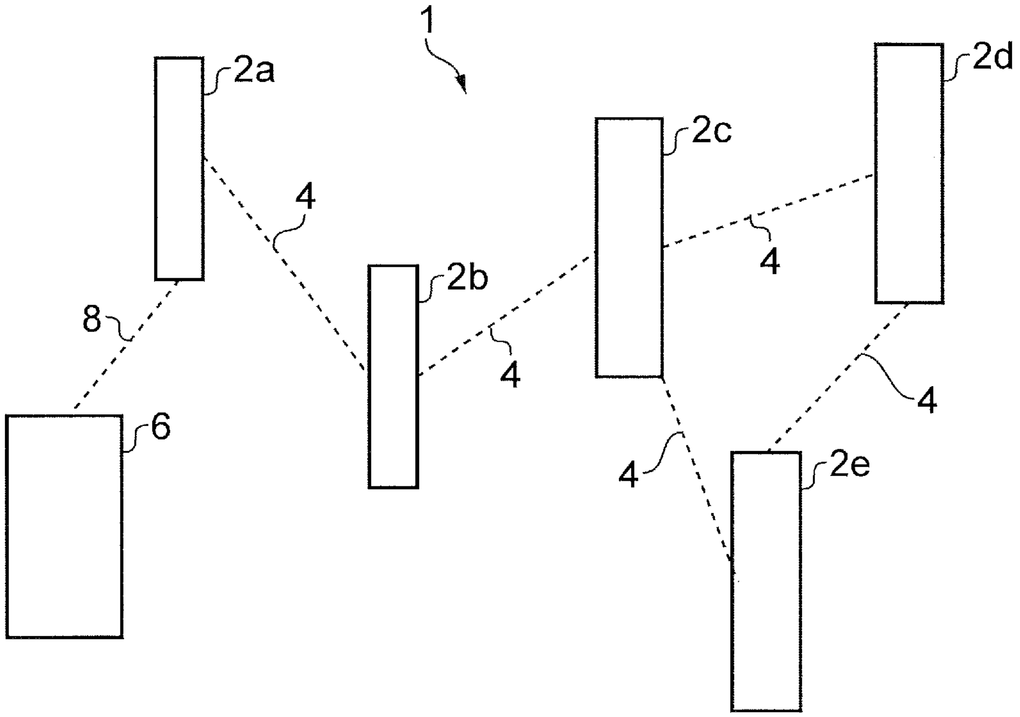
FIG. 2 schematically illustrates an example devices environment.

A first example of a devices environment 1 in which the present teachings can be utilized is shown in FIG. 2. In this example, a number of aerosol provision devices 2_a_ through 2_e_ are present in the devices environment 1. Various of the aerosol provision device 2 are interconnected via wireless links illustrated by dotted lines 4. However, not every aerosol provision device 2 is directly interconnected with each other aerosol provision device. Rather, the aerosol provision devices 2 are interconnected in a mesh-like pattern with a scatter net data flow. Thus, it can be seen that for a message to pass from aerosol provision device 2_a_ to aerosol provision device 2_d_, that message would be passed via aerosol provision devices 2_b_ and 2_c_ (and optionally also 2_e_) in order to reach aerosol provision device 2_d_. From some perspectives, it may be considered appropriate to describe these interactions as a PICONET as an alternative to using the description of meshing or meshed interaction. To provide for ease of readability this description will use the term mesh throughout.

To achieve such a mesh-like communication structure, a device consistent with the present teachings can take on more than one persona and thus can belong to more than one BTLE communication relationship and furthermore, the device can act as a central or a peripheral in one BTLE communication relationship and as a peripheral in another BTLE communication relationship. To manage the simultaneous nature of these different personas, the device of the present teachings can be operated to switch between the two personas, such that at any one time the device adopts only one persona. The switching back and forth between personas happens often enough that each communication relationship is maintained without the devices with which those communication relationships are formed concluding that the device has become unavailable and closing those communication relationships.

Switching between the personas within a given device would take place on a timescale consistent with the demands a particular application for the device. There is some random element to the switching, as illustrated with respect to FIG. 1 above. The time ranges within which the random element can operate would however be set in accordance with application demands. For example, to provide for rapid data transmission through a mesh of devices the persona switching would occur at relatively high frequency. For example in an implementation based upon interactions by devices associated with users in a transient location (such as where the devices are END devices in a social situation) then each device may be configured to switch roles every few seconds. On the other hand, for greater power efficiency and where data transmission speed through the mesh is of lower concern a relatively lower persona switching frequency can be used, perhaps dropping in a suitable context to switching roles only once or twice per hour. Also, the relative duration of peripheral and central roles can be altered according to the factors applicable to the implementation environment. Thus while the peripheral persona is active the device will send data as part of the advertising packet, and while the central persona is active the device will listen for devices advertising data packets.

Additionally, a device according to the present teachings can have multiple central personas, which can be used to communicate in different meshes or to increase the total number of peripherals with which it can hold bond relationships at any one time above a limit imposed by the particular Bluetooth chipset deployed. These multiple central personas can be implemented by using the persona switching approach outlined above, or by implementing multiple BTLE MCUs.

By using such a technique, for example, the interconnections between the aerosol provision devices 2 could occur in the form of aerosol provision device 2*a* acting as central and aerosol provision device 2*b* acting as peripheral in a first BTLE relationship. Aerosol provision device 2*b* may also act a central in a second BTLE relationship that features aerosol provision device 2*c* as a peripheral. Aerosol provision device 2*c* may in turn be the central in a third BTLE relationship that includes aerosol provision devices 2*d* and 2*e* as peripherals. Further, aerosol provision device 2*d* may be also be central in a fourth BTLE relationship that includes aerosol provision device 2*e* as a peripheral. As will be appreciated, other orderings of which aerosol provision devices function as central and peripheral in various possible aerosol provision device relationships can be implemented. For example, the connectivity shown in FIG. 1 could alternatively be provided by having aerosol provision device 2*b* function as central in a BTLE relationship in which aerosol provision devices 2*a* and 2*c* are peripherals, and by having aerosol provision device 2*d* function as central in a relationship in which aerosol provision device 2*c* is a peripheral, and by having aerosol provision device 2*e* function as central in a relationship in which aerosol provision devices 2*c* and 2*d* are peripherals. As will be seen from the discussion below, the arrangement of relationships to make up the mesh may be determined on an ad-hoc basis depending upon which aerosol provision devices become centrals as a result of the relationship establishment process.

The mesh approach set out in the present disclosure allows the passing of small data packets or tokens between aerosol provision devices without a need to establish full BTLE bond relationships between the aerosol provision devices. Thus such tokens may be flooded through a mesh of any two or more aerosol provision devices based upon transient or impermanent aerosol provision device to aerosol provision device relationships where the peripheral to central relationship lasts just long enough to transmit and receive the token. This approach does not prevent some or all of the aerosol provision devices in the mesh establishing bond relationships (also known as pairing). Such a bond-based approach may be used for example in circumstances where volumes of data larger than can be accommodated using tokens need to be transmitted between aerosol provision devices in the mesh.

As also illustrated in FIG. 2, an additional device 6 may be provided. The device 6 need have no knowledge or capability in respect of the meshable interconnectivity of the aerosol provision devices 2 and instead implements the communication protocol in a conventional way. For example, the device 6 implements a conventional BTLE interface and is able therefore to establish a connection 6 with one of the meshable aerosol provision devices 2 such that the device 6 acts as central and the aerosol provision device 2 acts as periphery. Alternatively, the device may utilize the same meshable interconnectivity in order to communicate with one or more of the aerosol provision devices 2.

Accordingly, it will be seen that the approach of the present teachings allows a Bluetooth or BTLE-based mesh to be established without a controlling device that provides a core node for a star-type topology. The mesh can interact with a non-meshed device, but this interaction can be either continuous or intermittent and the non-meshed device need not have any role in establishing, controlling or configuring the mesh.

Therefore, by establishing such a mesh network, the various aerosol provision devices 2 can communicate with each other and pass information on to other devices within range using an existing communication protocol such as BTLE. However, as will be appreciated from the discussion, the device uses a modified form of the Bluetooth hardware implementation with Generic Attribute Profile (GATT) Notification to achieve this ad-hoc meshable behavior. As will be appreciated from the present teachings, this modification can be achieved by implementing a modified hardware, firmware or software implementation of the protocol, for example by using an implementation of a controller circuit that complies in many respects with the standard communication protocol, but includes additional functionality provided for example using a script to achieve the device-to-device interactions described herein. The additional functionality may be introduced using modified hardware which, while this involves using non-standard hardware, does provide that the hardware could provide both modes on a full time basis without the need for time-divided sharing of the personas. The controller circuit may be a hardware circuit with functionality provided by its configuration, such as an application specific integrated circuit (ASIC) or may be a programmable microprocessor (μP) or microcontroller (MCU) operating under firmware and/or software control.

Figure 3:
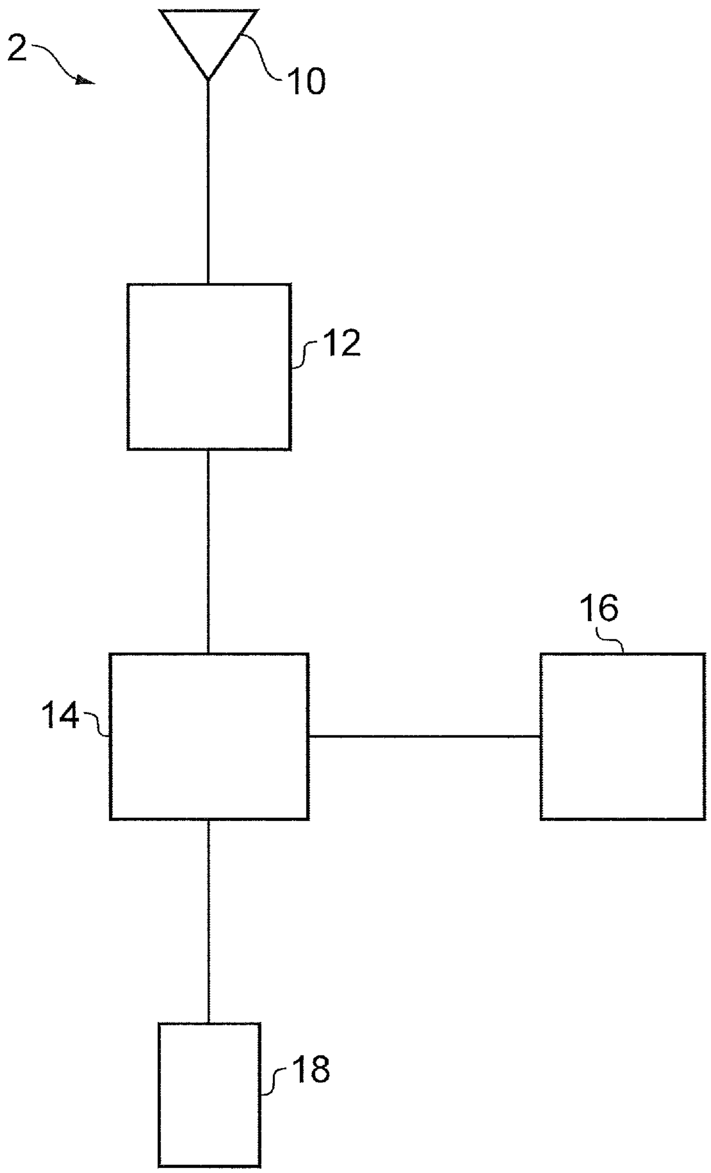
FIG. 3 schematically illustrates functional components of an aerosol provision device.

FIG. 3 illustrates schematically the functional components of each aerosol provision device 2. Each aerosol provision device 2 has an antenna 10 for transmitting and receiving BTLE signals. The antenna 10 is connected to a wireless communication interface 12, for example a BTLE control circuit 12 such as a BTLE MCU. The wireless communication interface 12 receives data for transmission from and provides received data to a device core functionality processor 14 which operates, for example in conjunction with memory 16 and/or I/O elements 18 to carry out the core computing functionality of the aerosol provision device 2. Although it has been shown in FIG. 3 that the functional components of the aerosol provision device 2 interact on an direct link basis, it will be understood that as FIG. 3 is schematic in nature, this description also includes alternative arrangements of the functional components, for example on a bus interconnect basis. It will also be appreciated that one or more of the functional components illustrated may be provided by a single physical component, and also that one functional component may be provided by multiple physical components.

With regard to the functional components relating to the core computing functionality of the aerosol provision device 2, it will be appreciated that the nature and usage of these components may differ depending upon the nature of the device itself. In the example of the aerosol provision device 2, the core computing functionality may include passing or information tokens between aerosol provision device devices, monitoring and reporting of device charge and/or nicotine fluid levels, lost and found interactions, and usage recording. Thus it will also be appreciated that the core computing functionality may differ from a user-perceived core functionality of the device. For example, in the case of an aerosol provision device, the user-perceived core functionality will likely be that of aerosol generation for nicotine delivery, with the computing functionalities being additional, supplementary or secondary to that user-perceived core functionality.

Figure 4:
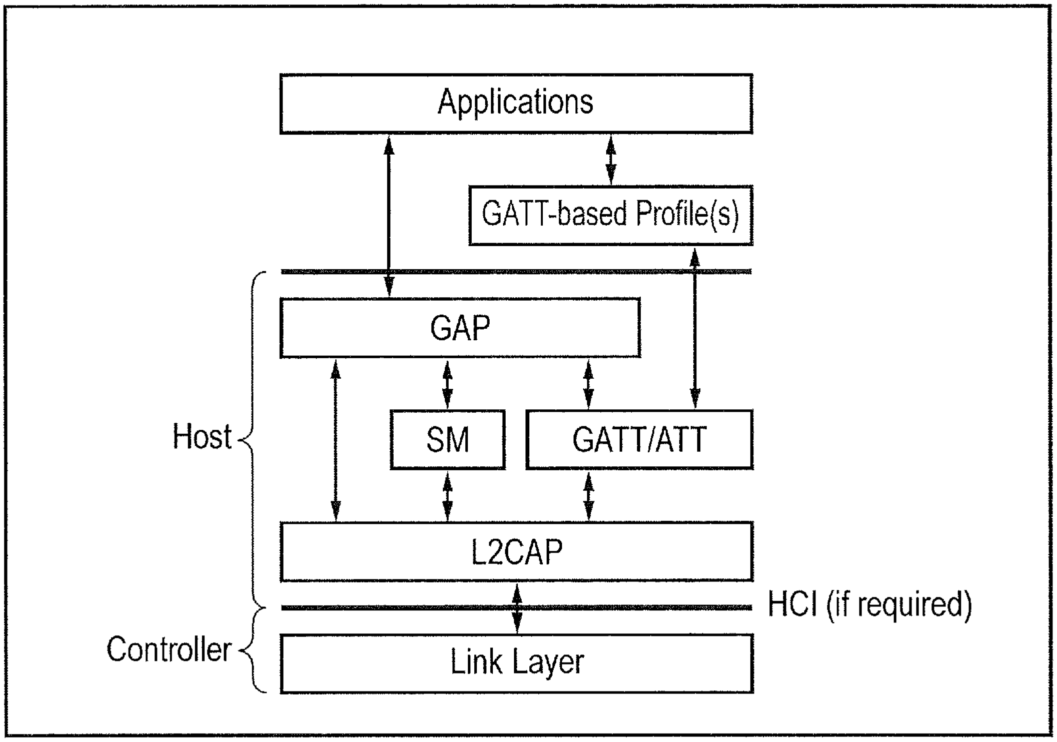
FIG. 4 schematically illustrates a protocol stack.

FIG. 4 then illustrates schematically a protocol structure as implemented by the wireless communication interface 12 of each aerosol provision device 2. The protocol structure illustrated in FIG. 4 corresponds to the Bluetooth stack, which includes the GATT (generic attribute protocol), GAP (generic access protocol), SM (service manager protocol), GATT/ATT (low energy attribute protocol), L2CAP (logical link control and adaptation layer), and link layer. In the present examples the link layer operates on a LERF (low energy radio frequency) basis. As illustrated in FIG. 4, the protocol stack can be conceptually divided between the so-called Host and Controller layers. The controller part is made up of the lower layers that are required for physical layer packets and associated timing. The controller part of the stack may be implemented in the form of an integrated circuit such as a SoC (system-on-a-chip) package with an integrated Bluetooth radio.

The layer implementations relevant to understanding the present teachings include the link layer, the L2CAP, the GAP and the low energy attribute protocol.

The link layer controller is responsible for low level communication over a physical interface. It manages the sequence and timing of transmitted and received frames, and using link layer protocol, communicates with other devices regarding connection parameters and data flow control. It also handles frames received and transmitted while the device is in advertising or scanner modes. The link layer controller also provides gate keeping functionality to limit exposure and data exchange with other devices. If filtering is configured, the link layer controller maintains a "white list" of allowed devices and will ignore all requests for data exchange or advertising information from others. As well as providing security functionality, this can also help manage power consumption. The link layer controller uses a host controller interface (HCI) to communicate with upper layers of the stack if the layer implementations are not co-located.

The logical link control and adaptation layer protocol (L2CAP) component provides data services to upper layer protocols like security manager protocol and attribute protocol. It is responsible for protocol multiplexing and data segmentation into small enough packets for the link layer controller, and de-multiplexing and reassembly operation on the other end. The L2CAP's has a backend interface is for the GAP that defines the generic procedures related to the discovery of BTLE devices and link management aspects of connecting to other BTLE devices. The GAP provides an interface for the application to configure and enables different modes of operation, e.g. advertising or scanning, and also to initiate, establish, and manage connection with other devices. The GAP is therefore used control connections and advertising in Bluetooth. GAP controls device visibility and determines how two devices can (or cannot) interact with each other.

The low energy attribute protocol (ATT) is optimized for small packet sizes used in Bluetooth low energy and allows an attribute server to expose a set of attributes and their associated values to an attribute client. These attributes can be discovered, read, and written by peer devices. The GATT provides a framework for using ATT.

As will be apparent from the discussions above, the present teachings use the advertising process to facilitate the meshed interaction of multiple devices, for example to permit scattering information between an unlimited number of devices for the purpose of disseminating data over distances and time.

Figure 5:
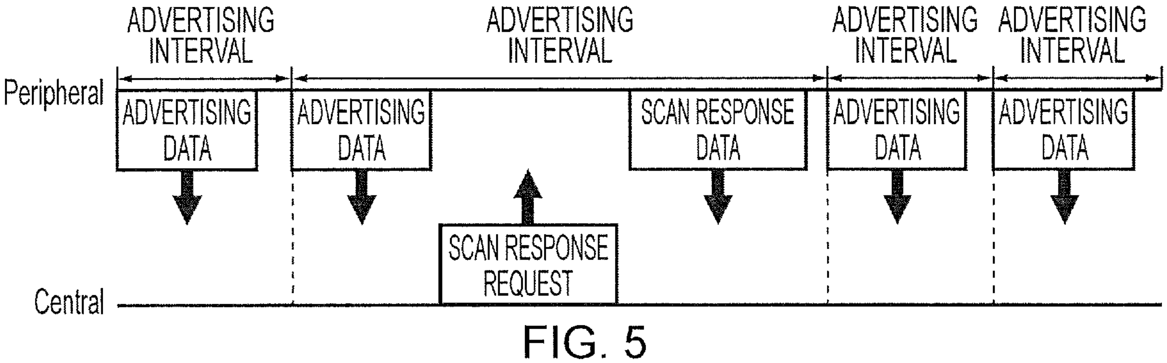
FIG. 5 schematically illustrates scan response timing.

In the context of the present examples, an application running on a device communicating via the meshed structure described herein may request or watch for specific scan response payloads, responsive to a scan response being sent by that device. This approach is used in conventional Bluetooth implementations to transmit the device name and other identification details. However in the present approaches, this scan response, which is defined as a 31 byte data packet, also referred to as a token, is used to share ID information related to a variable that when read by an application will trigger a particular response or action. The timing of such requests is illustrated in FIG. 5. As can be seen from this Figure, the scan response request is transmitted by the central device during the advertising interval and the scan response data is provided by the peripheral before the start of the next advertising interval.

By implementing the approach of the present teachings, data passing over the physical layer is indistinguishable at that level from ordinary BTLE traffic. Also, although higher-level layers are modified to accept the present meshable-interaction of devices, a non-meshable enabled application can communicate over BTLE using a device consistent with the present teachings.

Also, a device that utilizes only a conventional BTLE stack (such as device 6 illustrated in FIG. 2 above) can communicate with an aerosol provision device 2 that uses the meshable approach of the present teachings. The conventional BTLE device can then receive data from the meshable aerosol provision device 2 without the BTLE stack in the conventional BTLE device having any knowledge of the meshed interactions of the aerosol provision devices 2. The data that the conventional BTLE device receives may have originated at the directly connected aerosol provision device 2, or may have originated at aerosol provision device that previously connected to the directly connected aerosol provision device 2 via the mesh and which data has been stored or cached at the meshable aerosol provision device 2. The origin of such mesh-transferred data could be another meshed aerosol provision device 2, or could be another conventional BTLE device that is or has been connected to a meshed aerosol provision device.

Figure 6:
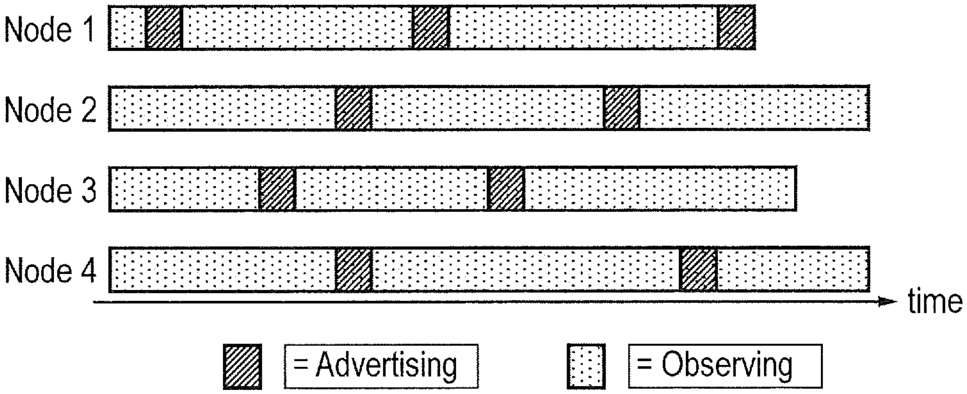
FIG. 6 schematically illustrates mode scheduling.

FIG. 6 illustrates schematically the behavior of each aerosol provision device 2 in relation to managing the dual persona nature of each aerosol provision device 2 to establish connections as both central and peripheral. As BTLE provides for two operating modes at the presentation layer, one corresponding to each of central and periphery roles, the aerosol provision device 2 of the present examples alternates between these two modes so as to provide for both advertiser broadcasting to advertise its capability as a peripheral and for observer activity to look for other peripheral-capable aerosol provision devices to which it can connect as central. While acting as observer, the aerosol provision device can act upon any received broadcaster advertisement to establish a connection as central in accordance with the usual BTLE conduct, for example as set out in the BTLE Generic Access Profile (GAP). While performing advertiser broadcasting, it will be able to establish a connection as peripheral with an observing aerosol provision device that responds to become a central. As is discussed above, this time-sharing between the personas of central and peripheral carries on after the connections between the devices have been established. This provides that the single device can operate in both modes on an ongoing, albeit time multiplexed, basis based upon a single BTLE MCU in the device.

Thus an aerosol provision device configured to provide the meshable-interaction of the present example uses the standard BTLE GATT (Generic Attribute Profile) specification in combination with a modified GAP to adopt the two operation modes associated with the dual-persona nature of the aerosol provision device. As will be discussed below, the aerosol provision device alternates between advertising as a peripheral and listening as a central so as to facilitate being able to connect to other aerosol provision devices in both central and peripheral modes. Typically the device already has an indication of the identity of the mesh in that the devices can be pre-programmed to use a particular UUID tied to the particular device mesh ("service" in BTLE terms) that the devices are intended to participate in. For example all END devices from a particular brand, range, or manufacturer may be programmed to use the same UUID. Within this context, to identify the active persona or mode, the aerosol provision device uses an ID code that uniquely identifies the aerosol provision device within the mesh. The ID and UUID (in effect mesh ID or group ID) codes are held in the firmware of the device and inserted into the advertising packets along with the data that makes up the token and may also be referenced in scan response requests and scan response messages as part of the advertising under GAP interactions with and between the devices.

While operating as a central, the aerosol provision device can adopt the states Scanner, Initiator and Master, and while operating as a peripheral the aerosol provision device can adopt the states Advertiser and Slave.

FIG. 6 also illustrates the relative advertising and observing times of multiple aerosol provision devices. The illustrated approach tends to avoid (but not necessarily exclude) multiple aerosol provision devices in range of one another performing broadcast simultaneously. In the present example, the duration of the observing period is controlled to fall in the range of 0.01 ms and 5 s, and the advertising period is of a fixed duration which may be in the range of 0.5 s to 10 s. In other examples, the advertising duration may also be variable and the observing duration may fall within a different range, overlapping range or subset of the example range given above. Such time offsetting can be achieved in a number of ways such as by coordination between the aerosol provision devices, or by each aerosol provision device using an interval length adjustment such as to provide uneven time spacing between each mode transition. Such interval length adjustments could be provided by selecting for each interval one of a number of possible interval lengths or by using some form of interval duration randomizer.

When an aerosol provision device is observing with a view to establishing a role as a central in a mesh, the aerosol provision device acts no differently to an aerosol provision device with no meshing capability when listening for advertisement from a potential peripheral aerosol provision device. Thus an aerosol provision device operating in this mode can also become a central to a conventional BTLE device without the meshing capability of the present teachings.

When an aerosol provision device is advertising with a view to establishing a role as a peripheral in a mesh, it advertises using a structure based upon the BTLE GAP data. However the BTLE GAP structure is modified to include mesh-specific information that can be recognized by a mesh-capable device which receives the advertisement. The mesh-specific information can include fields such as:

- the ID of the advertising aerosol provision device;
- packet sequence number of a packet awaiting transmission from that aerosol provision device, this is used to avoid duplicates—depending on the application, this may simply be a packet sequence of packets originated from that aerosol provision device (for example where the application requires only that the payload or token from the advertising aerosol provision device is flooded to multiple other aerosol provision devices) but could be made unique for a given mesh (group ID), time window and/or other uniqueness scope according to the application requirements;
- source aerosol provision device identifier of the packet having that packet sequence number, to reflect that the token now being passed may have originated at a different aerosol provision device to the one that is now passing it on;
- destination aerosol provision device identifier for the packet having that packet sequence number, depending on the implementation this can be a single aerosol provision device (corresponding to some form of routed operation) or 'all' aerosol provision devices (corresponding to flooding type operation);
- the group ID of the source aerosol provision device for the packet having that sequence number, which is used to allow multiple mesh networks to co-exist in the same physical space (as explained above, this group ID typically uses the BTLE UUID, although another group ID filed could be defined and used if required);
- life time or expiry time of the packet having that sequence number;
- payload, the data specific to a particular application—for example data relating to an END device application.

In accordance with the BTLE data handling approach, if a given application payload item is too large for a single packet, that payload item is broken down and distributed within multiple packets before reassembly at the/each destination aerosol provision device. In such applications a bond may be established between aerosol provision devices so as to provide for more transmission management for this larger data volume.

Figure 7:
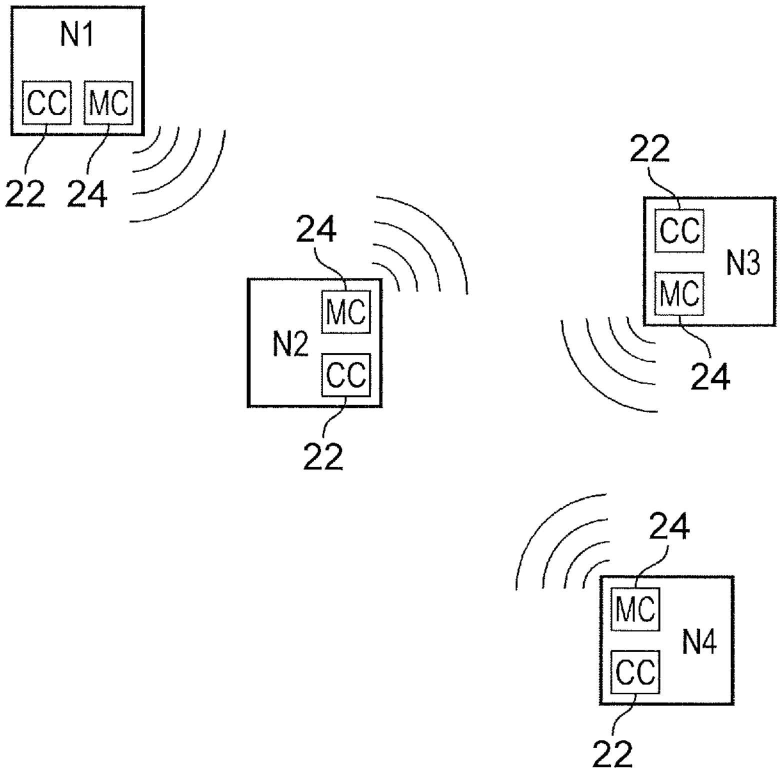
FIG. 7 schematically illustrates a mesh of aerosol provision devices.

FIG. 7 schematically illustrates connectivity patterns between a number of aerosol provision devices N1, N2, N3 and N4. In this illustration, aerosol provision device N1 is out of range for direct communication with aerosol provision device N4. Different operation modes of the aerosol provision devices are signified by the elements control chip (CC) 22 and mesh chip (MC) 24 of each of aerosol provision devices N1 to N4. The control chip is representative of the aerosol provision device MCU operating to communicate with a conventional BTLE device such as the device 6 shown in FIG. 2. The mesh chip is representative of the aerosol provision device MCU operating in both central and peripheral modes to communicate through the mesh.

In the example of FIG. 7, aerosol provision device N1 has a bit set in an advertisement data field indicating that it has data to send. The schedule of advertising and observing in each aerosol provision device causes aerosol provision device N2 to be the first aerosol provision device in direct communication range with N1 to listen as a central following aerosol provision device N1 having the advertisement data field set. Thus aerosol provision device N2 when in central mode receives the advertising data which N1 is advertising while in peripheral mode. This advertising data, as received by N2 can be used by N2 in connection with an application running at or otherwise associated with N2. In addition or alternatively, aerosol provision device N2 can cache the advertising data ready for onward transmission as advertising data on a future occasion that aerosol provision device N2 adopts its peripheral persona. Thereby, the advertising data that originated at N1 can pass onward from N2 as advertising data that it then received by aerosol provision device N3 at a time when N2 is advertising as peripheral and N3 is listening as central. The advertising data that originated with N1 can then be used and/or passed on by N3, ultimately arriving at N4 by the same method.

It should be noted that in this implementation, the advertising data is effectively flooded across the mesh. Thus, if N1 happens to be listening as central at the same time that N2 is advertising as peripheral, the advertising data will return to N1 as well as passing onward through the mesh to N3. In this circumstance either the aerosol provision device N1 or some application running at or associated with N1 may simply discard the returning advertising data. In some implementations, the aerosol provision device or application may make use of the returned advertising data in some way, for example using the time between transmission and receipt as some form of random interval generator or for mesh diagnostics.

As has been explained above, it is possible for the transmission over the mesh to be in the more structured format of using established bonds between the aerosol provision devices. In such a circumstance, each pair of aerosol provision devices will interact over an established bond and the persona switching at each aerosol provision device will provide for data received in a bond of which one persona is a member can then be onwardly transmitted using a bond of which the other persona is a member.

Control as to whether the data is transmitted to every aerosol provision device (flooding) or whether the data is transmitted only to selected aerosol provision devices (routing) can be achieved in several ways. If the data is to be automatically communicated to all aerosol provision devices without restriction, then this can be a default state configured into the aerosol provision devices. If the data is to be transmitted only to aerosol provision devices currently active in the mesh, then this can be achieved either as default behavior set in the aerosol provision devices or on an application-specific basis where the application is mesh-aware and provides control information to the communication stack to indicate the data transmission extent. If the data is only to be transmitted to specific aerosol provision devices, this can be achieved on an application-specific basis where the application is mesh-aware and provides control information to the communication stack to indicate the data transmission extent. The present examples are configured to operate on the basis of a flooding approach such that data is automatically forwarded to all presently-meshed devices.

Figure 8:
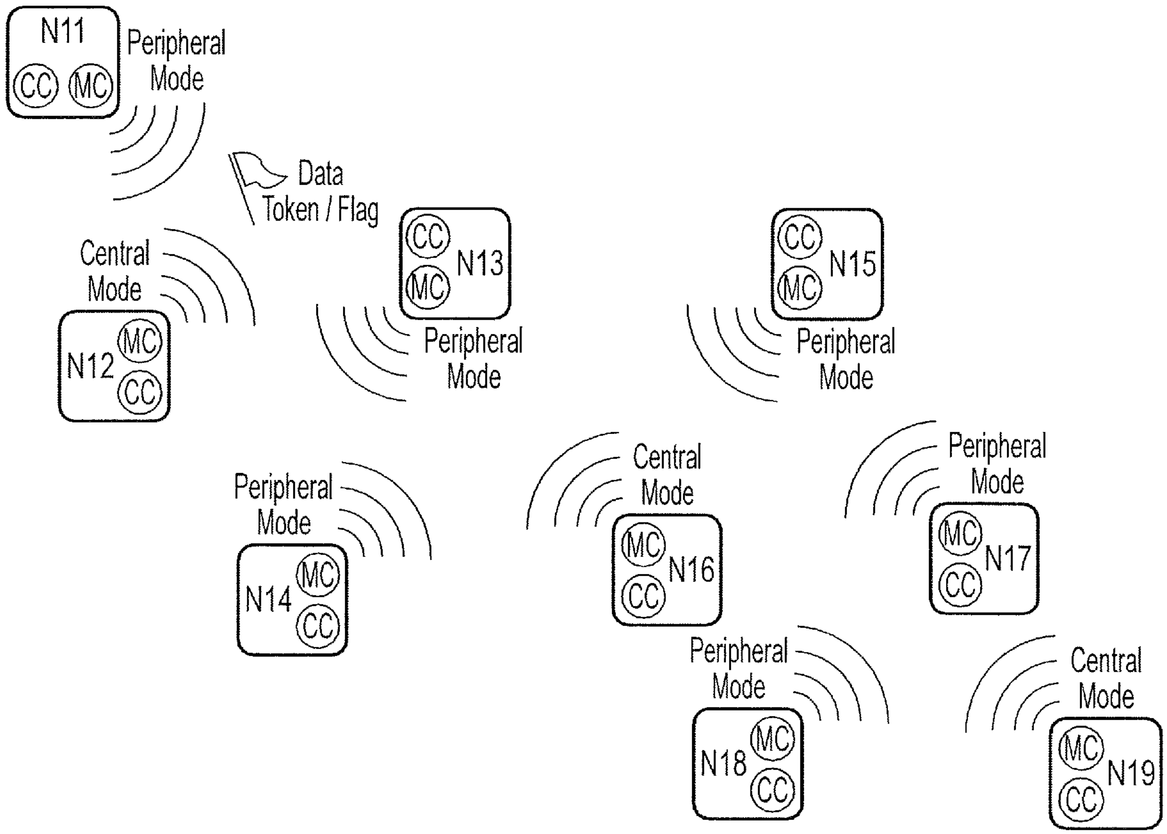
FIG. 8 schematically illustrates a mesh of aerosol provision devices.

FIG. 8 provides a further illustration of meshing behavior as between aerosol provision devices. In this example, a larger number of aerosol provision devices N11 to N19 are present. The illustration in FIG. 8 represents a given snapshot in time such that different ones of the aerosol provision devices are illustrated as having currently adopted different ones of their respective peripheral and central personas. At the time illustrated in FIG. 8 three aerosol provision devices have become configured into central mode, these being aerosol provision devices N12, N16 and N19, with the remaining aerosol provision devices having become configured into peripheral mode. As will be appreciated from the discussion above, for any given instance of the same aerosol provision devices being present in the same locations, the exact number and identify of the aerosol provision devices that become configured into the central mode will depend upon factors such as the scheduling by each aerosol provision device of its advertising/observing periods and the relative location of each aerosol provision device compared to any other aerosol provision device that has already become configured into either central or peripheral mode. The passing of a data token is illustrated in the figure by the presence of a flag passing from N11 sending this data token in its advertising data to N12 which will receive that advertising data listening in central mode. This token will later be included in advertising data from N12 when N12 adopts its peripheral persona. Thereby the token can be passed onward through the mesh and ultimately arrive at each aerosol provision device in the mesh at least once.

As will be understood from the discussion above, the meshes can change dynamically based upon changes to the numbers and positions of aerosol provision devices in the mesh. For example as aerosol provision devices move away from the remainder of the mesh, eventually they will lose contact with all aerosol provision devices in the mesh and leave the mesh. Likewise, an aerosol provision device that is deactivated or enters a power saving non-wireless mode will lose contact with the other aerosol provision devices in the mesh and leave the mesh. Further, new aerosol provision devices not previously a part of the mesh will be able to join the mesh as and when they come within range of an aerosol provision device in the mesh or when they are powered while within range of an aerosol provision device in the mesh. Also, as will be understood from the discussion of persona switching above, an aerosol provision device already within the mesh and operating as a peripheral within the mesh will also operate at a different time as a central within the mesh. In an implementation in which the mesh adopts bond relationships such that particular aerosol provision devices have defined roles as centrals in some bonds and peripherals in others, if an aerosol provision device then changes location relative to the aerosol provision devices in the mesh it may in effect leave the mesh as all established bonds may cease to operate of the range to the new location. Such an aerosol provision device would then resume attempting both observing and advertising until it establishes one or more new bond relationships into other aerosol provision devices of the bond-linked mesh.

As the skilled reader will appreciate, Bluetooth and BTLE provide for securing of an inter-node communication bond. This is not applicable to the purely advertising-based transmission of tokens in the form of advertising data unless such transmission of tokens leads to the establishment of bond relationships. In the present examples, even where bond relationships are used, the aerosol provision devices can be configured to establish such bonds without requiring user input to confirm trust between the different aerosol provision devices or other devices. Rather, in the present examples, aerosol provision devices of a particular type can be configured to pre-trust all other aerosol provision devices of that particular type. For example, each aerosol provision device can be configured to trust all other devices that identify as being aerosol provision devices from a given manufacturer, group of manufacturers, brand, group of brands, model, group of models or as being compliant with a given aerosol provision device standard or group of standards.

Such a trust pattern can be supplemented with inherent controls on the amount of personal data that the device stores/is permitted to transmit. For example, an aerosol provision device may be configured by the owning user to not hold or to be prevented from sharing any information that identifies the owner. This would not preclude the END device from interacting with other END devices to pass on information that can be used for lost/found functionality or from passing on information about the END device itself to provide for group interactions between END devices of the same brand or model, for example as discussed below.

In other examples, trust may be a user-explicit functionality, such that a user may be required to actively accept or request a communication bond to be established with another aerosol provision device.

Where a particular aerosol provision device or other device is being configured by the user, for example to communicate with a conventional BTLE device of the user such as a smartphone, phablet or tablet device, the trust relationship between the user's meshable device and conventional BTLE device may be secured in the same manner as other conventional BTLE pairings to establish a communication bond.

Thus it will be understood that by using the approach of the present teachings, a device can be provided that is capable of meshed interaction with other similar devices by adopting a dual-persona structure in which the device is able to operate on a time-division basis as both a master (central) and slave (peripheral) for communication with those other like devices while also operating as a slave/peripheral to a conventional device without the dual persona capability.

This approach can be used to facilitate device-to-device interactions between a range of devices for a range of purposes. As discussed above, examples of devices that can be equipped for such device-to-device interactions using the meshed or PICONET topology approach of the above examples include electronic nicotine delivery devices (END devices).

The meshable interconnectivity of the aerosol provision devices 2A and one or more other devices as described above may be considered a connectionless-state interaction, wherein connectionless-state packets are created, transmitted and received by each device in accordance with the examples described above with reference to FIGS. 1 to 8.

In an example system, an aerosol provision device 2*a* is configured to operate a wireless communication interface 12 in a listening mode. In other words, as described above, for the given aerosol provision device 2*a*, the central persona is active such that the aerosol provision device 2*a* will listen for other devices' advertising data packets. Whilst operating in the listening mode, the aerosol provision device 2*a* may receive data in the form of one or more data packets from the wireless communication interface of another aerosol provision device 2*b*. In this example system, the data received from the other aerosol provision device 2*b* is transmitted by the other aerosol provision device 2*b* as part of an advertising packet. Alternatively, an advertising packet may be transmitted by the other aerosol provision device 2*b* and in response, the aerosol provision device 2*a* transmits a connectionless-state request packet to the other aerosol provision device 2*b*. The data received from the other aerosol provision device 2*b* is then transmitted to the aerosol provision device 2*a* as part of a connectionless-state response packet.

The data received from the other aerosol provision device 2*b* includes information describing usage characteristics of the other aerosol provision device 2*b*. For example, the usage characteristics may comprise one or more values selected from the group comprising: battery properties, aerosol generation properties, aerosol medium properties, aerosol generation event properties, and erroneous or abnormal behavior properties.

Battery properties may include the current charge state of the battery of the aerosol provision device 2*b*, the last time the battery was charged, the number of charging cycles the battery has undergone, the duration of the last charging cycle, the average duration of a charging cycle, and the battery threshold before charging is required.

Aerosol generation properties may include the average puff duration, the total puff duration, the total puff count, the number of puffs per power profile (e.g., the number of puffs for a high power profile and a number of puffs for a low power profile), the currently selected power profile, and the average number of times per day the aerosol provision device 2*b* is used.

Aerosol medium properties may include the type and/or flavor of cartomizer currently being used, and the type and/or flavor of the cartomizer used most often with the aerosol provision device 2*b*.

Aerosol generation event properties may include the average boot or uptime time for the aerosol provision device 2*b*, the average boot or uptime time, the last time an overheat protection mode was triggered, and the number of times an overheat protection mode has been triggered.

Erroneous or abnormal behavior properties may include error codes generated by the aerosol provision device 2*b*, for example the number of times that a puff received from a user was too short for the aerosol provision device to generate a response from the device (e.g., no aerosol was generated), the time each error code was generated, and details of any abnormal or unexpected behavior from the aerosol provision device 2*b*.

The usage characteristics of the respective aerosol provision device are recorded and stored in the memory during use of the respective aerosol provision device. For example, aerosol provision device 2*b* generates the usage characteristics during use of the aerosol provision device 2*b* and stores the generated usage characteristics in its own memory before transmitting the usage characteristics in a data packet to aerosol provision device 2*a*. Equally, aerosol provision device 2*a* generates its own usage characteristics during use of the aerosol provision device 2*a* and stores its generated usage characteristics in memory 16.

In the present example, the data received from the other aerosol provision device 2*b* optionally includes information about the aerosol provision device 2*b*, such as the product type, batch number, serial number and/or UUID of the aerosol provision device 2*b* (or more generally any information identifying the aerosol provision device 2*b*), and the location of the aerosol provision device 2*b* when the data was transmitted by the aerosol provision device 2*b*, for example in the form of GPS coordinates or a map grid reference.

The aerosol provision device 2*a* stores the data received from the other aerosol provision device 2*b* in its memory 16. The data may also be timestamped in order to record when the data was received from the other aerosol device 2*b*. The processor 14 of the aerosol provision device 2*a* may also determine whether the location of the aerosol provision device 2*b* when the data was transmitted by the aerosol provision device 2*b* is included in the received data and, if not, the processor 14 may edit the received data to include the location of the aerosol provision device 2*a* when the data was received, for example in the form of GPS coordinates or a map grid reference. Once the predetermined amount of time, such as 1 hour, 24 hours, or 7 days, has elapsed since the data was stored in the memory 16, the data may be deleted from the memory 16.

In the present example, prior to storing the received data in memory 16, the processor 14 of the aerosol provision device 2*a* optionally determines whether data from that particular aerosol provision device 2*b* has already been stored in the memory 16, for example by searching the received data for the serial number and/or UUID of the aerosol provision device 2*b* it was received from and searching the memory 16 for data associated with the same serial number and/or UUID. If it is determined that data from that particular aerosol provision device 2*b* is already stored in the memory 16, the processor 14 of the aerosol provision device 2*a* may be configured to overwrite the data from that particular aerosol provision device 2*b* that is already stored in the memory 16 with the data most recently received from that particular aerosol provision device 2*b*. Alternatively, the processor 14 of the aerosol provision device 2*a* may be configured to discard the data most recently received from that particular aerosol provision device 2*b*, or append the data most recently received from that particular aerosol provision device 2*b* to the data received from that particular aerosol provision device 2*b* already stored in the memory 16. For example, if the data already stored in the memory 16 is from a first time period and the most recently received data is from a second, different, time period, the most recently received data can be appended to the data already stored in the memory 16 in order to provide further resolution and granularity of usage characteristics for the aerosol provision device 2*b*.

In the present example, the aerosol provision device 2*a* may be configured to store data from a predetermined number of aerosol provision devices in its memory 16, for example 5 or 10 devices. Accordingly, prior to storing the received data in memory 16, the processor 14 of the aerosol provision device 2*a* determines the number of aerosol provision devices from which data has been previously received and stored in the memory 16 of the aerosol provision device 2*a*, for example by searching the data for the serial number and/or UUID of the aerosol provision device it was received from and counting the number of unique serial numbers or UUIDs that exist in the memory 16. If it is determined that the number of aerosol provision devices from which data has been previously received is less than the predetermined number, the processor 14 of the aerosol provision device 2*a* is configured to store the data received from the other aerosol provision device 2*b* in its memory 16. If it is determined that the number of aerosol provision devices from which data has been previously received is greater than or equal to the predetermined number, the processor 14 of the aerosol provision device 2*a* is configured to determine the oldest data packet in the memory 16, for example by examining the timestamp associated with each data packet to find the data packet with the least recent timestamp, thereby indicating that the data packet was stored in the memory 16 least recently. The processor 14 is then configured to delete the data packet that the processor 14 has determined to be the oldest and the data received from the other aerosol provision device 2*b* is stored in memory 16 in place of the deleted data packet. In a further example, the aerosol provision device 2*a* may have a maximum storage limit for storing data with the maximum number of devices about which data can be stored being limited by the size of the stored data about each device. In this example, the same general principles of deleting oldest stored data may be applied using a test of available remaining storage in place of (or in addition to) number of devices about which data has previously been received and stored.

Whilst operating in the listening mode, the aerosol provision device 2*a* may receive data from the respective wireless communication interfaces of multiple aerosol provision devices, for example aerosol provision devices 2*b-e*. In such an example, the aerosol provision device 2*a* is configured to receive data from a single aerosol provision device, determine whether to store the received data and store the received data if required as described before continuing to receive data from the next aerosol provision device. The process may be repeated for each data packet received from another aerosol provision device as long as the wireless communication interface 12 of the aerosol provision device 2*a* is operating in the listening mode. Optionally, the wireless communication interface 12 of the aerosol provision device 2*a* is configured to operate in the listening mode by default, and will operate in the listening mode unless otherwise configured by the processor 14 of the aerosol provision device 2*a*.

The examples described above, in which an aerosol provision device 2*a* receives and stores data from other aerosol provision devices, allow the aerosol provision device 2*a* to collect data from any other aerosol provision device that it comes into transmission range of, for example up to 1 m, 10 m, 100 m or more.

The wireless communication interface 12 of the aerosol provision device 2*a* is used to create a connectionless-state advertising packet that includes information relating to an identity and advertising state of the aerosol provision device 2*a*. The information relating to the identity of the aerosol provision device 2*a* may include the serial number and/or UUID of the aerosol provision device 2*a*. The connectionless-state advertising packet is then transmitted via the via the wireless communication interface 12.

In response to transmitting the connectionless-state advertising packet, a connectionless-state request packet from a remote wireless device 6 is received via the wireless communication interface 12. The remote wireless device 6 may be a mobile communications device, such as a mobile phone, smartphone, phablet or tablet device, a host or gateway device or a beacon, such as a BLE beacon. The mobile communications device 6 may have a particular application installed to enable communication with an aerosol provision device.

In response to receiving the request packet, the processor 14 of the aerosol provision device 2*a* is configured to create, using the wireless communication interface 12, a connectionless-state response packet and transmit the response packet via the wireless communication interface 12.

At least one of the advertising packet and the response packet includes the received data from the memory 16 and data generated by the aerosol provision device 2*a* and stored in the memory 16. In the present example, the data generated by the aerosol provision device 2*a* includes information describing usage characteristics of the aerosol provision device 2*a*. For example, the usage characteristics may comprise one or more values selected from the group comprising: battery properties, aerosol generation properties, aerosol medium properties, aerosol generation event properties, and erroneous or abnormal behavior properties. The data generated by the aerosol provision device 2*a* may include the same information as the data received from another aerosol provision device 2*b* or may include different information. For example, the data received from another aerosol provision device 2*b* may only comprise aerosol generation event properties for that particular aerosol provision device 2*b* whilst the data generated by aerosol provision device 2*a* may include usage characteristics for the aerosol provision device 2*a*, including values for each of battery properties, aerosol generation properties, aerosol medium properties, aerosol generation event properties, and erroneous or abnormal behavior properties. The processor 14 of the aerosol provision device 2*a* may also determine the location of the aerosol provision device 2*a* at the time when the data is to be transmitted and edit the data to be transmitted to include the location of the aerosol provision device 2*a*, for example in the form of GPS coordinates or a map grid reference.

In the present example, the at least one of the advertising packet and the response packet which includes the received data from the memory 16 and data generated by the aerosol provision device 2*a* and stored in the memory 16 optionally does not include all of the received data stored in the memory 16. For example, the processor 14 of the aerosol provision device 2*a* may be configured to send all of the data stored in the memory 16 relating to usage characteristics of its own aerosol provision device 14, but only a selection of the received data stored in the memory 16. The selection may comprise only selected values, such as only battery properties or only aerosol medium properties, or may comprise values from each of the group of usage characteristics but with less granularity such that less than all of the received data is stored in the memory 16. For example, if the received data comprises 10 values for error codes generated by the aerosol provision device 2*b*, the processor 14 may be configured to only include 2 to 5 of the values for the error codes in the transmitted data packet. Alternatively or in addition, the processor 14 may be configured to only include, for example, every second, third, tenth or hundredth value for each or a particular usage characteristic. The processor may be configured to only include, for example, 10 values for each usage characteristic. The processor is then configured to determine the number of values for each usage characteristic in the received data and divide this by 10 in order to determine the interval from which the values should be taken. Alternatively, the processor 14 may be configured to only take one or more of the average, maximum, minimum, medium and/or modal value for each usage characteristic. The processor 14 may also be configured to include in the data to be stored and/or transmitted any values which represent anomalies or outliers. For example, the processor 14 may be configured to include the average value for a given usage characteristic, along with any value which is above or below a predetermined value, for example two standard deviations larger or smaller than the average value.

The examples described above provide that the remote wireless device 6 is able to receive data which has originated from multiple different aerosol provision devices 2*a*, 2*b* whilst only having to interact with a single aerosol provision device 2*a*. This allows the remote wireless device to receive data from multiple aerosol provision devices whilst only being in transmission range of a single aerosol provision device. The remote wireless device 6 may be fixed in particular location, such as on the wall of a building or billboard. The remote wireless device 6 is then able to receive data directly from any aerosol provision device which comes into transmission range of the remote wireless device 6, whilst the received data may have originated from multiple different aerosol provision devices. The remote wireless device 6 is therefore able to capture data from multiple different aerosol provision devices which the remote wireless device 6 has not come into transmission range of. Further, the consumer or owner of each aerosol provision device 2*a* is unaware of any transmissions or receiving of data occurring.

The remote wireless device 6 stores the data received from an aerosol provision device 2*a* in memory associated with remote wireless device 6. Alternatively, the remote wireless device 6 may be an intermediary device, and may collate and transmit data received from aerosol provision devices to another device using a conventional wireless communication protocol, such as Bluetooth, Bluetooth Low Energy, WiFi or through a cellular network.

As described above in relation to when the aerosol provision device 2*a* receives data from another aerosol provision device 2*b*, the remote wireless device 6 may timestamp the received data in order to record when the data was received from the aerosol provision device 2*a*. The remote wireless device 6 may also determine whether the location of the aerosol provision device 2*a* when the data was transmitted by the aerosol provision device 2*a* is included in the received data and, if not, the remote wireless device 6 may edit the received data to include the location of the remote wireless device 6 when the data was received, for example in the form of GPS coordinates or a map grid reference. Optionally, once the predetermined amount of time, such as 1 hour or 24 hours, has elapsed since the data was stored in the memory of the remote wireless device 6, the data is deleted from the memory of the remote wireless device 6.

Optionally, prior to storing the received data in memory of the remote wireless device 6, the remote wireless device 6 determines whether data for any of the aerosol provision devices included in the received data has already been stored in the memory remote wireless device 6, for example by searching the received data for the serial number and/or UUID of each aerosol provision device it originated from and searching the memory of the remote wireless device 6 for data associated with the same serial number and/or UUID. If it is determined that data from a particular aerosol provision device is already stored in the memory of the remote wireless device 6, the remote wireless device 6 may be configured to overwrite the data originating from that particular aerosol provision device that is already stored in the memory with the data most recently received and originating from that particular aerosol provision device. Alternatively, the remote wireless device 6 may be configured to discard the data most recently received and originating from that particular aerosol provision device, or append the data most recently received and originating from that particular aerosol provision device to the data originating from that particular aerosol provision device already stored in the memory. For example, if the data already stored in the memory of the remote wireless device 6 is from a first time period and the most recently received data is from a second, different, time period, the most recently received data can be appended to the data already stored in the memory of the remote wireless device 6 in order to provide further resolution and granularity of usage characteristics for the particular aerosol provision device.

Location data for each aerosol provision device in the data received by the remote wireless device 6 can be used to determine the movement of each aerosol provision device and their corresponding owner. For example, if each packet of data from a particular aerosol provision device 2*a* contains location information and a timestamp, the remote wireless device 6 can generate a history of where the aerosol provision device 2*a* was at particular points in time and determine whether any patterns exist, such as if the aerosol provision device 2*a* was at a particular location at the same time each day of the week, thereby suggesting a place of work or home of the owner of the aerosol provision device 2*a*. In another example, the devices from which data has originating in each data packet received by the remote wireless device 6 can be used to determine any interaction patterns between individual aerosol provision devices. For example, if each data packet received by the remote wireless device 6 from a particular aerosol provision device 2*a* always or regularly includes data originating from another particular aerosol provision device 2*b*, the remote wireless device 6 may determine that the users of those particular two aerosol provision devices 2*a*, 2*b* are friends or colleagues who regularly interact with one another, or that the users of those particular two aerosol provision devices 2*a*, 2*b* live in a similar location and regularly pass each other. Location information and timestamps associated with the data from each aerosol provision device can also be used to assist in this determination.

FIG. 9 illustrates a method for an aerosol provision device. At S9-1, the wireless communication interface 12 of the aerosol provision device 2*a* is configured to operate in a listening mode. At S9-2, the wireless communication interface 12 of the aerosol provision device 2*a* receives data from the wireless communication interface of another aerosol provision device 2*b*. At S9-3, the received data is stored in the memory 16 of the aerosol provision device 2*a*. At S9-4, a connectionless-state advertising packet that includes information relating to an identity and advertising state of the aerosol provision device 2*a* is created using the wireless communication interface 12 of the aerosol provision device 2*a*. At S9-5, the advertising packet is transmitted via the wireless communication interface 12. At S9-6, a connectionless-state request packet from a remote wireless device 6 is received via the wireless connection interface 12 of the aerosol provision device 2*a*. At S9-7, the connection interface 12 of the aerosol provision device 2*a* is used to create a connectionless-state response packet and at S9-8 the response packet is transmitted via the wireless communication interface 12 of the aerosol provision device 2*a*. In this implementation, at least the response packet includes the received data from the other aerosol provision device 2*b* which is stored in the memory 16 of the aerosol provision device 2*a* and data generated by the aerosol provision device 2*a* which is also stored in the memory 16 of the aerosol provision device 2*a* (although the received data may also be included in the advertising packet).

It should be appreciated that although it has been described and shown that S9-4 to S9-8 occur after S9-1 to S9-3, S9-4 to S9-8 may occur at any time in relation to S9-1 to S9-3. That is, for example, the connectionless-state advertising packet may be generated and transmitted on a periodic basis and this may be before or after the aerosol provision device 2*a* receives data from the wireless communication interface of another aerosol provision device 2*b*.

The illustrated method above focuses on the transmission of response packets from the aerosol provision device 2*a*. However, it should be appreciated that aerosol provision device 2*b* (or any other aerosol provision device) may transmit response packets to wireless device 6. For example, prior to S9-6, the wireless device 6 identifies aerosol provision devices that are within range of the wireless device 6 (e.g., by measuring the signal strength of the advertising packets transmitted in S9-5 and determining that an aerosol provision device is within range if the measured signal strength is greater than or equal to a threshold value). Accordingly, the wireless device 6 transmits connectionless-state request packets to the identified aerosol provision devices (that may be via a broadcast or unicast signal). Each aerosol provision device subsequently receives the connectionless-state request packet at S9-6 and each aerosol provision device follows S9-7 and S9-8. The wireless device 6 subsequently receives connectionless-state response packets from the aerosol provision devices.

Additionally, it should also be appreciated that the transmission of the connectionless-state request packet from wireless device 6 may not be triggered by reception of the advertising packet of S9-5 by the wireless device 6. Instead, the wireless device 6 may periodically transmit a connectionless-state request packet which triggers any aerosol provision device that receives the connection-less state request packet to transmit its connectionless-state response packet (that is, to perform S9-7). In this case, prior to S9-7, the aerosol provision device determines whether it is in range of the wireless device 6 (e.g., by measuring the signal strength of the request packet transmitted from the wireless device 6 and determining that an aerosol provision device is within range if the measured signal strength is greater than or equal to a threshold value).

Additionally, it should be appreciated that in other implementations, S9-5 to S9-8 may be omitted. For example, if the advertising packet generated at S9-4 includes the received data from aerosol provision device 2*b*, after S9-5 the transmitted advertising packet is received by the wireless device 6. The wireless device 6 is configured to identify (and optionally store) the received data relating to aerosol provision device 2*b* in addition to the data relating to aerosol provision device 2*a* from the advertising packet.

Figure 10:
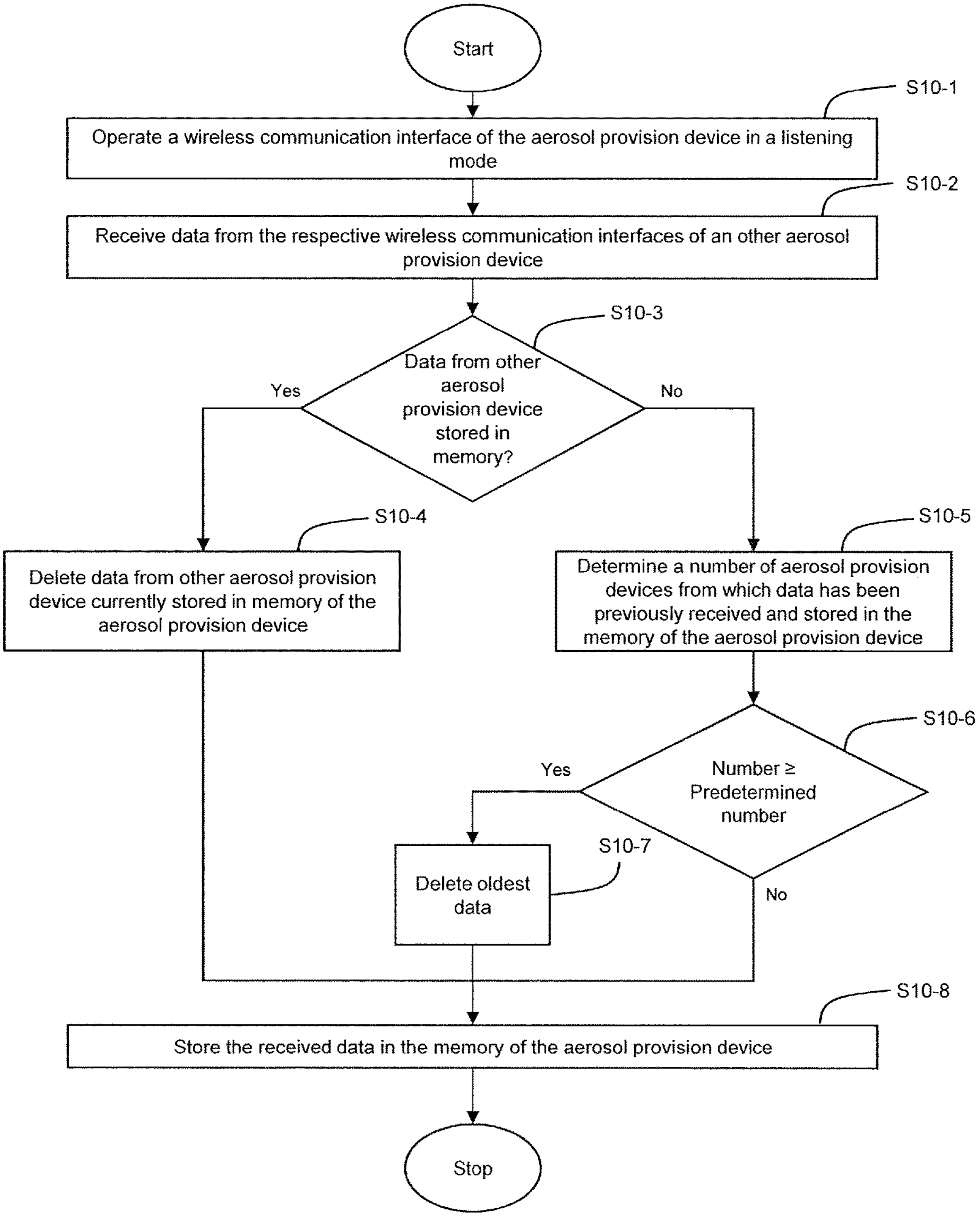
FIG. 10 schematically illustrates a method for an aerosol provision device.

FIG. 10 illustrates a method for an aerosol provision device which optionally forms part of the method illustrated in FIG. 9. As can be seen from FIG. 10, S10-1, S10-2 and S10-8 of the method illustrated in FIG. 10 correspond, respectively, to S9-1, S9-2 and S9-3 of the method illustrated in FIG. 9. Accordingly, following completion of S10-8, the method may continue onto S9-4 of the method illustrated in FIG. 9. Alternatively, the method illustrated in FIG. 10 is repeated until a predetermined time before the method continues onto S9-4 of the method illustrated in FIG. 9. At S10-1, the wireless communication interface 12 of the aerosol provision device 2*a* is configured to operate in a listening mode. At S10-2, the wireless communication interface 12 of the aerosol provision device 2*a* receives data from the wireless communication interface of another aerosol provision device 2*b*. At S10-3, it is determined whether data from the other aerosol provision device 2*b* is currently stored in the memory 16 of the aerosol provision device 2*a*, for example the processor 14 of the aerosol provision device 2*a* may be configured to search the received data for the serial number and/or UUID of the aerosol provision device 2*b* it was received from and searching the memory 16 for data associated with the same serial number and/or UUID. If it is determined that data from that other aerosol provision device 2*b* is currently stored in the memory 16 of the aerosol provision device 2*a*, the method continues to S10-4, where the data from the other aerosol provision device 2*b* currently stored in the memory 16 of the aerosol provision device 2*a* is deleted. The method then continues to S10-8, where the received data is stored in the memory 16 of the aerosol provision device 2*a*.

Alternatively, if at S10-3 it is determined that data from that other aerosol provision device 2*b* is not currently stored in the memory 16 of the aerosol provision device 2*a*, the method continues to S10-5, where the number of aerosol provision devices from which data has been previously received and stored in the memory of the aerosol provision device is determined. For example, the processor 14 of the aerosol provision device 2*a* may be configured to determine the number of aerosol provision devices from which data has been previously received and stored in the memory 16 of the aerosol provision device 2*a* by searching the data for the serial number and/or UUID of the aerosol provision device it was received from and counting the number of unique serial numbers or UUIDs that exist in the memory 16. The method the proceeds to S10-5, where it is determined whether the number of aerosol provision devices from which data has been previously received and stored in the memory 16 of the aerosol provision device 2*a* is greater than or equal to a predetermined number. If it is determined that the number of aerosol provision devices from which data has been previously received and stored in the memory 16 of the aerosol provision device 2*a* is greater than or equal to the predetermined number, the method continues to S10-7, where the oldest data is deleted from the memory 16 of aerosol provision device 2*a*. For example, the processor 14 of the aerosol provision device 2*a* may be configured to examine a timestamp associated with each data packet stored in the memory 16 of aerosol provision device 2*a* in order to determine which of the data packets is the oldest. The processor 14 is then configured to delete the data packet that is determined to be the oldest. The method then continues to S10-8, where the received data is stored in the memory 16 of the aerosol provision device 2*a*. Alternatively, if at S10-3 it is determined that the number of aerosol provision devices from which data has been previously received and stored in the memory 16 of the aerosol provision device 2*a* is less than the predetermined number, the method continues directly to S10-8, where the received data is stored in the memory 16 of the aerosol provision device 2*a*.

The method illustrated in FIG. 10 thereby limits the amount of data that is stored in the memory 16 of the aerosol provision device 2*a*, whilst ensuring that only the most recent data from each other aerosol provision device is stored in the memory 16 of the aerosol provision device 2*a*. This also reduces the amount of memory required in the aerosol provision device 2*a*.

When the method illustrated in FIG. 10 is continued with the method illustrated in FIG. 9, this ensures that the data transmitted to the remote wireless device 6 is from the most recent interactions with other aerosol devices. This also limits the amount of data that needs to be transmitted to the remote wireless device 6, thereby reducing the power consumption requirements for the aerosol provision device and reducing the amount of time it takes to transmit the data. This increases the likelihood that the data will be successfully received by the remote wireless device 6 whilst the aerosol provision device 2*a* and the remote wireless device 6 are within transmission range of one another, for example up to 1 m, 10 m, 100 m or more. For example, a consumer may be carrying the aerosol provision device 2*a* in their hand or pocket, and the aerosol provision device 2*a* is able to transmit data to the remote wireless device 6 whilst the consumer walks or otherwise travels past and within transmission range of the remote wireless device 6, without the consumer being aware of an interaction occurring.

Therefore, from one perspective, there has been described a method for an aerosol provision device. The method comprises operating a wireless communication interface of the aerosol provision device in a listening mode. During operation of the listening mode, data is received data from the wireless communication interface of another aerosol provision device. The received data is stored in a memory of the aerosol provision device. A connectionless-state advertising packet that includes information relating to an identity and advertising state of the aerosol provision device is created using the wireless communication interface of the aerosol provision device and transmitted via the wireless communication interface. A connectionless-state request packet is received from a remote wireless device, via the wireless communication interface. In response to receiving the request packet, a connectionless-state response packet is created using the wireless communication interface and the response packet is transmitted via the wireless communication interface. At least one of the advertising packet and the response packet includes the received data from the memory and data generated by the aerosol provision device and stored in the memory.

It should be appreciated that although the embodiments described above have been primarily described in relation to a wireless communication interface that uses Bluetooth LE, the principles of the present disclosure are not limited to using a particular wireless communication interface. For example, other implementations may be based on a Wi-Fi direct communication interface, or any other radio communication interface.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the disclosure scope defined by the claims or limitations on equivalents to the claims, and that other embodiments may be utilized and modifications may be made without departing from the scope and/or spirit of the claims.

Further examples consistent with the present teachings are set out in the following numbered clauses:

[Clause 1] A method for an aerosol provision device, the method comprising:

operating a wireless communication interface of the aerosol provision device in a listening mode;

during operation of the listening mode, receiving data from the wireless communication interface of an other aerosol provision device;

storing the received data in a memory of the aerosol provision device;

creating, using the wireless communication interface of the aerosol provision device, a connectionless-state advertising packet that includes information relating to an identity and advertising state of the aerosol provision device;

transmitting the advertising packet via the wireless communication interface;

receiving a connectionless-state request packet from a remote wireless device, via the wireless communication interface;

responsive to receiving the request packet, creating, using the wireless communication interface, a connectionless-state response packet; and transmitting the response packet via the wireless communication interface, wherein at least one of the advertising packet and the response packet includes the received data from the memory and data generated by the aerosol provision device and stored in the memory.

[Clause 2] The method of clause 1, wherein the data includes information describing usage characteristics of the respective aerosol provision device.

[Clause 3] The method of clause 2, wherein the usage characteristics of the respective aerosol provision device comprises one or more values selected from the group comprising: battery properties, aerosol generation properties, aerosol medium properties, aerosol generation event properties, and erroneous or abnormal behavior properties.

[Clause 4] The method of clause 2 or clause 3, wherein the usage characteristics of the respective aerosol provision device are recorded and stored in the memory during use of the respective aerosol provision device.

[Clause 5] The method of any one of clauses 1 to 4, wherein the at least one of the advertising packet and the response packet which includes the received data from the memory and data generated by the aerosol provision device and stored in the memory includes a selection of the received data stored in the memory and all of the data generated by the aerosol provision device and stored in the memory.

[Clause 6] The method of any one of clauses 1 to 4, wherein the at least one of the advertising packet and the response packet which includes the received data from the memory and data generated by the aerosol provision device and stored in the memory includes a selection of the received data stored in the memory and the data generated by the aerosol provision device and stored in the memory.

[Clause 7] The method of clause 5 or clause 6, wherein the selection comprises information relating to a particular usage characteristic of the respective aerosol provision device.

[Clause 8] The method of clause 5 or clause 6, wherein the selection comprises storing less than all of the received data.

[Clause 9] The method of any one of clauses 1 to 8, further comprising:

deleting, prior to storing the received data in a memory of the aerosol provision device, any data previously received from the other aerosol provision device and stored in the memory of the aerosol provision device.

[Clause 10] The method of any one of clauses 1 to 9, further comprising:

determining, prior to storing the received data in a memory of the aerosol provision device, a number of aerosol provision devices from which data has been previously received and stored in the memory of the aerosol provision device; and if the number of aerosol provision devices from which data has been previously received is greater than or equal to a predetermined number, deleting at least the oldest data prior to storing the data received from the other aerosol provision device.

[Clause 11] The method of any one of clauses 1 to 10, wherein the data generated by the aerosol provision device and/or the data received from the other aerosol provision device includes location data for the respective aerosol provision device.

[Clause 12] The method of any one of clauses 1 to 11, wherein the at least one of the advertising packet and the response packet which includes the received data from the memory and data generated by the aerosol provision device and stored in the memory includes a timestamp.

[Clause 13] The method of any one of clauses 1 to 12, further comprising:

deleting, after a predetermined period of time, the received data stored in the memory of the aerosol provision device.

[Clause 14] The method of any one of clauses 1 to 13, wherein the wireless communication interface is a Bluetooth low energy communication interface.

[Clause 15] An aerosol provision device comprising:

a processor a wireless communication interface;

memory containing instructions which, when executed by the processor, performs the method of any one of clauses 1 to 14.

[Clause 16] A wireless device comprising:

a processor a wireless communication interface;

memory containing instructions which, when executed by the processor, performs a method comprising:

operating the wireless communication interface in a listening mode;

during operation of the listening mode, receiving, from an aerosol provision device, an advertising packet, via the wireless communication interface;

transmitting, to the aerosol provision device, a connectionless-state request packet, via the wireless communication interface;

receiving, from the aerosol provision, a connectionless-state response packet via the wireless communication interface, wherein at least one of the advertising packet and the response packet includes data generated by the aerosol provision device and data received by the aerosol provision device another aerosol provision device.

Various embodiments of the claimed scope may suitably comprise, consist of, or consist essentially of, appropriate combinations of the disclosed elements, components, features, parts, steps, means, etc, other than those specifically described herein. In addition, this disclosure may include other concepts not presently claimed, but which may be claimed in future either in combination with or separately to the presently claimed features.

The invention claimed is:

1. A method for an aerosol provision device, the method comprising:

- operating a wireless communication interface of the aerosol provision device in a listening mode;
- during operation of the listening mode, receiving data from the wireless communication interface of an other aerosol provision device;
- storing the received data in a memory of the aerosol provision device;
- creating, using the wireless communication interface of the aerosol provision device, a connectionless-state advertising packet that includes information relating to an identity and an advertising state of the aerosol provision device;
- transmitting the advertising packet via the wireless communication interface;
- receiving a connectionless-state request packet from a remote wireless device, via the wireless communication interface;
- responsive to receiving the request packet, creating, using the wireless communication interface, a connectionless-state response packet; and
- transmitting the response packet via the wireless communication interface,
- wherein at least one of the advertising packet and the response packet includes the received data from the memory and data generated by the aerosol provision device and stored in the memory;
- and wherein the method further comprises:
- determining, prior to storing the received data in the memory of the aerosol provision device, a number of aerosol provision devices from which data has been previously received and stored in the memory of the aerosol provision device; and
- if the number of aerosol provision devices from which data has been previously received is greater than or equal to a predetermined number, deleting at least the oldest data prior to storing the data received from the other aerosol provision device.

2. The method of claim 1, wherein the received data includes information describing usage characteristics of the other aerosol provision device.

3. The method of claim 2, wherein the usage characteristics of the other aerosol provision device comprise one or more values of: battery properties, aerosol generation properties, aerosol medium properties, aerosol generation event properties, and erroneous or abnormal behavior properties.

4. The method of claim 2, wherein the usage characteristics of the other aerosol provision device are recorded and stored in the memory during use of the other aerosol provision device.

5. The method of claim 1, wherein the at least one of the advertising packet and the response packet which includes the received data from the memory and data generated by the aerosol provision device and stored in the memory includes a selection of the received data stored in the memory and all of the data generated by the aerosol provision device and stored in the memory.

6. The method of claim 1, wherein the at least one of the advertising packet and the response packet which includes the received data from the memory and data generated by the aerosol provision device and stored in the memory includes a selection of the received data stored in the memory and the data generated by the aerosol provision device and stored in the memory.

7. The method of claim 5, wherein the selection comprises information relating to a particular usage characteristic of the other aerosol provision device.

8. The method of claim 5, wherein the selection comprises storing less than all of the received data.

9. The method of claim 1, further comprising:

deleting, prior to storing the received data in a memory of the aerosol provision device, any data previously received from the other aerosol provision device and stored in the memory of the aerosol provision device.

10. The method of claim 1, wherein at least one of the data generated by the aerosol provision device or the data received from the other aerosol provision device includes location data for the respective aerosol provision device.

11. The method of claim 1, wherein the at least one of the advertising packet and the response packet which includes the received data from the memory and data generated by the aerosol provision device and stored in the memory includes a timestamp.

12. The method of claim 1, further comprising:

deleting, after a predetermined period of time, the received data stored in the memory of the aerosol provision device.

13. The method of claim 1, wherein the wireless communication interface is a Bluetooth low energy communication interface.

14. An aerosol provision device comprising:

a processor;

a wireless communication interface; and memory containing instructions which, when executed by the processor, performs the method of claim 1.

* * * * *